US008623906B2

(12) United States Patent
Wu et al.

(10) Patent No.: US 8,623,906 B2
(45) Date of Patent: Jan. 7, 2014

(54) CARBOXY ISATIN HYDRAZONES AND THEIR ESTERS AS SHP2 INHIBITORS

(75) Inventors: Jie Wu, Tampa, FL (US); Nicholas James Lawrence, Tampa, FL (US); Said M. Sebti, Tampa, FL (US); Harshani Rithma Lawrence, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 13/274,699

(22) Filed: Oct. 17, 2011

(65) Prior Publication Data

US 2012/0034186 A1 Feb. 9, 2012

Related U.S. Application Data

(63) Continuation of application No. PCT/US2010/031506, filed on Apr. 16, 2010.

(60) Provisional application No. 61/170,354, filed on Apr. 17, 2009.

(51) Int. Cl.
*A61K 31/404* (2006.01)
*C07D 209/34* (2006.01)

(52) U.S. Cl.
USPC .......................................... 514/419; 548/483

(58) Field of Classification Search
USPC .......................................................... 548/483
See application file for complete search history.

(56) References Cited

U.S. PATENT DOCUMENTS

2003/0004351 A1   1/2003   Davis et al.

FOREIGN PATENT DOCUMENTS

| WO | 03024969 A1 | 3/2003 |
| WO | 03037252 A2 | 5/2003 |
| WO | 2006055187 A1 | 5/2006 |
| WO | 2009135000 A2 | 11/2009 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Cancer [online], [retrieved on Jul. 6, 2007]. Retrieved from the internet, URL; http://en.wikipedia.org|wiki|Cancer.*
Lawrence, et al. (2008) retrieved from CAPLUS; Document No. 149:298765.*
Preliminary Report on Patentability for PCT/US2010/031506 dated May 30, 2011.
Alonso et al. 2004. Protein tyrosine phophatases in the human genome. Cell. vol. 117. pp. 699-711.
Baron et al. 2008. Inhibition of IFN-gamma-induced STAT1 tyrosine phosphorylation by human CMV is mediated by SHP2. J. Immunol. vol. 181. pp. 5530-5536.
Bentires-ALJ et al. 2004. Activating mutations of the noonan syndrome-associated SHP2/PTPN11 gene in human solid tumors and adult acute myelogenous leukemia. Cancer Res. vol. 64. pp. 8816-8820.
Bialy et al. 2005. Inhibitors of protein tyrosine phosphatases: next-generation drugs? Angew. Chem. Int. Ed. Engl.vol. 44. pp. 3814-3839.
Blume-Jensen et al. 2001. Oncogenic kinase signalling. Nature. vol. 411. pp. 355-365.
Boutros et al. 2007. CDC25 phosphatases in cancer cells: key players? Good targets? Nat. Rev. Cancer. vol. 7. pp. 495-507.
Boutselis et al. 2007. Synthesis and cell-based activity of a potent and selective protein tyrosine phosphatase 1B inhibitor prodrug. J. Med. Chem. vol. 50. pp. 856-864.
Chen et al. 2006. Discovery of a novel shp2 protein tyrosine phosphatase inhibitor. Mol. Pharmacol. vol. 70. pp. 562-570.
Chin et al. 1996. Cell growth arrest and induction of cyclin-dependent kinase inhibitor p21 WAF1/CIP1 mediated by STAT1. Science. vol. 272. pp. 719-722.
Cunnick et al. 2001. Phosphotyrosines 627 and 659 of Gab1 constitute a bisphosphoryl tyrosine-based activation motif (BTAM) conferring binding and activation of SHP2. J. Biol. Chem. vol. 276. No. 26. pp. 24380-24387.
Cunnick et al. 2002. Regulation of the mitogen-activated protein kinase signaling pathway by SHP2. J. Biol. Chem. vol. 277. No. 11. pp. 9498-9504.
Deininger et al. 2005. The development of imatinib as a therapeutic agent for chronic myeloid leukemia. Blood. vol. 105. pp. 2640-2653.
Fraley et al. 2004. Optimization of the indoyl quinolinone class of KDR (VEGFR-2) kinase inhibitors: effects of 5-amido- and 5-sulphonamido-indolyl groups on pharmocokinetics and hERG binding. Bioorg. & Med. Chem. Letters. vol. 14. pp. 351-355.
Fuchikawa et al. 2009. Protein tyrosine phosphatase SHP2 is involved in Semaphorin 4D-induced axon repulsion. Biochem. Biophys. Res. Commun. vol. 385. pp. 6-10.
Geronikaki et al. 2008. 2-Thiazolylimino/heteroarylimino-5-arylidene-4-thiazolidinones as new agents with SHP-2 inhibitory action. J. Med. Chem. vol. 51. pp. 5221-5228.
Hellmuth et al. 2008. Specific inhibitors of the protein tyrosine phosphatase Shp2 identified by high-throughput docking. Proc. Natl. Acad. Sci. U S A. vol. 105. No. 20. pp. 7275-7280.
Herschhorn, et al. 2007. De Novo parallel design, synthesis and evaluation of inhibitors against the reverse transcriptase of human immunodeficiency virus type-1 and drug-resistant variants. J. Med. Chem. vol. 50. pp. 2370-2384.
Hof et al. 1998. Crystal structure of the tyrosine phosphatase SHP-2. Cell. vol. 92. pp. 441-450.

(Continued)

*Primary Examiner* — Shawquia Young
(74) *Attorney, Agent, or Firm* — Robert J. Varkonyi; Smith & Hopen, P.A.

(57) ABSTRACT

Protein tyrosine phosphatase (PTP) Shp2 is a non-receptor PTP that involved in cell signaling and regulation of cell proliferation, differentiation, and migration. Shp2 mediates activation of kinases that are involved in the pathogenesis of human carcinoma. A high throughput screen identified compounds that inhibit the PTP Shp2. Several compounds were identified that selectively inhibit Shp2 over Shp1 with low to sub-micromolar activity. Also disclosed are methods of inhibiting a protein tyrosine phosphatase in a cell and treating cancer through selective inhibition of Shp2.

5 Claims, 19 Drawing Sheets

(56) References Cited

OTHER PUBLICATIONS

Jiang et al. 2008. Targeting PTPs with small molecule inhibitors in cancer treatment. Cancer Metastasis Rev. vol. 27. No. 2. pp. 263-272.
Johnston et al. 2009. Cdc25B dual-specificity phosphatase inhibitors identified in a high-throughput screen of the NIH compound library. Assay Drug Dev. Technol. vol. 7. pp. 250-265.
Joss et al. 1998. Interpreting kinetic rate constants from optical biosensor data recorded on a decaying surface. Anal. Biochem. vol. 261. pp. 203-210.
Keilhack et al. 2005. Diverse biochemical properties of Shp2 mutants. Implications for disease phenotypes. J. Biol. Chem. vol. 280. No. 35. pp. 30984-30993.
Lawrence et al. 2008. Inhibitors of Src homology-2 domain containing protein tyrosine phosphatase-2 (Shp2) based on oxindole scaffolds. J. Med. Chem. vol. 51. pp. 4948-4956.
Lee et al. 2001. Potent and selective nonpeptide inhibitors of caspases 3 and 7. J. Med. Chem. vol. 44. pp. 2015-2026.
Luo et al. 2009. Principles of cancer therapy: oncogene and nononcogene addiction. Cell. vol. 136. pp. 823-837.
Manes et al. 1999. Concerted activity of tyrosine phosphatase SHP-2 and focal adhesion kinase in regulation of cell motility. Mol. Cell. Biol. vol. 19. No. 4. pp. 3125-3135.
Mohi et al. 2007. The role of Shp2 (PTPN11) in cancer. Curr. Opin. Genet. & Dev. vol. 17. pp. 23-30.
Muller et al. 1998. Tandem immobilized metal-ion affinity chromatography/immunoaffinity purification of His-tagged proteins—evaluation of two anti-His-tag monoclonal antibodies. Anal. Biochem. vol. 259. pp. 54-61.
Mulloy et al. 2007. Epidermal growth factor receptor mutants from human lung cancers exhibit enhanced catalytic activity and increased sensitivity to gefitinib. Cancer Res. vol. 67. pp. 2325-2330.
Neel et al. 2003. The 'Shp'ing news: SH2 domain-containing tyrosine phosphatases in cell signaling. Trends Biochem. Sci. vol. 28. No. 6. pp. 284-293.
Nordin et al. 2005. Kinetic studies of small molecule interactions with protein kinases using biosensor technology. Anal. Biochem. vol. 340. pp. 359-368.
Noren-Muller et al. 2006. Discovery of protein phosphatase inhibitor classes by biology-oriented synthesis. Proc. Natl. Acad. Sci. USA. vol. 103. No. 28. pp. 10606-10611.
Ren et al. 2004. Roles of Gab1 and SHP2 in paxillin tyrosine dephosphorylation and Src activation in response to epidermal growth factor. J. Biol. Chem. vol. 279. No. 9. pp. 8497-8505.
Ren et al. 2007. Shp2(E76K) mutant confers cytokine-independent survival of TF-1 myeloid cells by up-regulating Bcl-X(L). J. Biol. Chem. vol. 282. No. 50. pp. 36463-36473.
Ribble et al. 2005. A simple technique for quantifying apoptosis in 96-well plates. BMC Biotechnol. vol. 5. No. 12. pp. 1-17.
Salmond et al. 2006. SHP2 forecast for the immune system:fog gradually clearing. Trends Immunol. vol. 27. No. 3. pp. 154-160.
Popp. 1969. Synthesis of potential antineoplastic agents XX. Compounds related to the 3-o-nitrophenylhydrazone of Isatin. Notes. vol. 12. pp. 182-184.
Stephens et al. 2005. PRL phosphatases as potential molecular targets in cancer. Mol. Cancer Ther. vol. 4. pp. 1653-1661.
Tartaglia et al. 2005. Germ-line and somatic PTPN11 mutations in human disease. Eur. J. Med. Genet. vol. 48. pp. 81-96.
Tenev et al. 1997. Both SH2 domains are involved in interaction of SHP-1 with the epidermal growth factor receptor but cannot confer receptor-directed activity to SHP-1/SHP-2 chimera. J. Biol. Chem. vol. 272. No. 9. pp. 5966-5973.
Tonks et al. 2007. A brake becomes an accelerator: PTP1B—a new therapeutic target for breast cancer. Cancer Cell. vol. 11. pp. 214-216.
Vadlamudi et al. 2002. Differential regulation of components of the focal adhesion complex by heregulin: role of phosphatase SHP-2. J. Cell. Physiol. vol. 190. pp. 189-199.
Wu et al. 2002. SHP-2 is a dualspecificity phosphatase involved in Stat1 dephosphorylation at both tyrosine and serine residues in nuclei. J. Biol. Chem. vol. 277. No. 49. pp. 47572-47580.
O'Reilly et al. 1998. Structural determinants of SHP-2 function and specificity in *Xenopus* mesoderm induction. Mol. Cell. Biol. vol. 18. No. 1. pp. 161-177.
Yang et al. 1998. Crystal structure of the catalytic domain of protein-tyrosine phosphatase SHP-1. J. Biol. Chem. vol. 273. No. 43. pp. 28199-28207.
Yang et al. 2003. Crystal structure of human protein-tyrosine phosphatase SHP-1. J. Biol. Chem. vol. 278. No. 8. pp. 6516-6520.
You et al. 1999. Shp-2 tyrosine phosphatase functions as a negative regulator of the interferon-stimulated Jak/STAT pathway. Mol. Cell. Biol. vol. 19. No. 3. pp. 2416-2424.
Goodwin et al. 2000. Synthesis of (13)C,(2)H(3)-Salmeterol: An analytical internal standard for pharmacokinetic studies. J. Labelled Cpd. Radiopharm. vol. 43. pp. 65-75.
Borror et al. 1988. Regioselectivity of electrophilic aromatic substitution: Syntheses of 6- and 7-Sulfamoylindolines and -indoles. J. Org. Chem. vol. 53. pp. 2047-2052.
Zhan et al. 2009. The protein tyrosine phosphatase SHP-2 is required for EGFRvIII oncogenic transformation in human glioblastoma cells. Exp. Cell. Res. vol. 315. No. 14. pp. 2343-2357.
Zhou et al. 2009. Molecular mechanism for SHP2 in promoting HER2-induced signaling and transformation. J. Biol. Chem. vol. 284. No. 18. pp. 12226-12234.
Manne, Veeraswamy, et al., "Bisubstrate Inhibitors of Farnesyltransferase: A Novel Class of Specific Inhibitors of RAS Transformed Cells", Oncogene, vol. 10, pp. 1763-1779, 1995.
Streiber, Martina, et al., "Methyl Esters of N-(Dicyclohexyl)acetyl-piperidine-4-(benzylidene-4-carboxylic acids) as Drugs and Prodrugs: A New Strategy for Dual Inhibition of 5Alpha-Reductase Type 1 and Type 2", Journal of Pharmaceutical Sciences, vol. 94, No. 3, Mar. 2005, Germany.
Zhao, Xiaotao T., et al., "Regulation of ACh Receptor Clustering by the Tyrosine Phosphatase Shp2", Developmental Neurobiology, pp. 1789-1801, 2007.
X. Zhou, et al., SHP2 is up-regulated in breast cancer cells and in infiltrating ductal carcinoma of the breast, implying its involvement in breast oncogenesis. Histopathology 2008, 53, pp. 389-402.
Liwei Chen, et al., Inhibition of cellular Shp2 activity by a methyl ester analog of SPI-112. Biochemical Pharmacology, 80, (2010) pp. 801-810.
Nicola Aceto, et al., Tyrosine Phosphatase SHP2 promotes breast cancer progression and maintains tumor-initiating cells via activation of key transcription factors and a positive feedback signaling loop. Nature Medicine, vol. 18, No. 4, Apr. 2012, pp. 529-538.
Liwei Chen, et al., Discovery of a Novel Shp2 Protein Tyrosine Phosphatase Inhibitor. Molecular Pharmacology, vol. 70, No. 2, (2006), pp. 562-570.
Michaela Scherr, et al., Enhanced sensitivity to inhibition of SHP2, STAT5, and Gab2 expression in chronic myeloid leukemia (CML). Blood, vol. 107, (2006) pp. 3279-3287.
Hideaki Higashi, et al., SHP-2 Tyrosine Phosphatase as an Intracellular Target of *Helicobacter pylori* CagA Protein. Science, vol. 295, (2002), pp. 683-686.
Megumi Higuchi, et al., Conditional gene silencing utilizing the lac repressor reveals a role of SHP-2 in cagA-positive *Helicobacter pylori* pathogenicity. Cancer Science, vol. 95, No. 5, May 2004, pp. 442-447.
Yi Zhan, et al., The protein tyrosine phosphatase SHP-2 is required for EGFRvIII oncogenic transformation in human glioblastoma cells. Experimental Cell Research, vol. 315, (2009) pp. 2343-2357.
L-M Sturla, et al., Src homology domain-containing phosphatase 2 suppresses cellular senescence in glioblastoma. British Journal of Cancer (2011) vol. 105, pp. 1235-1243.
SC Nabinger, et al., The protein tyrosine phosphatase, Shp2, positively contributes to FLT3-ITD-induced hematopoietic progenitor hyperproliferation and malignant disease in vivo. Leukemia (2012) pp. 1-11.
Suzanne Schubbert, et al., Functional analysis of leukemia-associated PTPN11 mutations in primary hematopoietic cells. Blood, vol. 106, No. 1, (2005) pp. 311-317.
Yuan Ren, et al., Critical Role of Shp2 in Tumor Growth Involving Regulation of c-Myc. Genes and Cancer, (2010) vol. 1, No. 10, pp. 994-1007.

(56) References Cited

OTHER PUBLICATIONS

HLA Win Piazza, et al., Enhanced anti-melanoma efficacy of interferon alfa-2b via inhibition of Shp2. Cancer Letters vol. 320 (2012) pp. 81-85.

Gordon Chan, et al., Leukemogenic Ptpn11 causes fatal myeloproliferative disorder via cell-autonomous effects on multiple stages of hematopoiesis. Blood, vol. 113 (2009) pp. 4414-4424.

Yuan Ren, et al., Shp2E76K Mutant Confers Cytokine-independent Survival of TF-1 Myeloid Cells by Up-regulating Bcl-XL. The Journal of Biological Chemistry, (2007), vol. 282, No. 50, pp. 36463-36473.

Gomes EG, et al., Targeting the Yin and the Yang: Combined Inhibition of the Tyrosine Kinase c-Src and the Tyrosine Phosphatase SHP-2 Disrupts Pancreatic Cancer Signaling and Biology In Vitro and Tumor Formation In Vivo. Pancreas. Jul. 2013, vol. 42, No. 5, pp. 795-806.

Mohamed Bentires-ALJ, et al., Activating Mutations of the Noonan Syndrome-Associated SHP2/PTPN11 Gene in Human Solid Tumors and Adult Acute Myelogenous Leukemia.Cancer Research, (2004) vol. 64, pp. 8816-8820.

Dan Xu, et al., Non—lineage/stage-restricted effects of a gain-of-function mutation in tyrosine phosphatase Ptpn11 (Shp2) on malignant transformation of hematopoietic cells. Journal of Experimental Medicine, vol. 208, No. 10 (2011) pp. 1977-1988.

X-D Zhou, et al., Inhibition of SHP2 leads to mesenchymal to epithelial transition in breast cancer cells. Cell Death and Differentiation (2008) vol. 15, pp. 988-996.

\* cited by examiner

A

CDL 4340-0580
$IC_{50}$ (Shp2): 2.2 µM

B

NA T6-297775
$IC_{50}$ (Shp2): 2.5 µM

JHE-02-035A
IC$_{50}$ : 7.8 μM

A

JHE-02-032A
IC$_{50}$ : 2.4 μM

B

JHE-02-032B
IC$_{50}$ : 4.8 μM

CARBOXY ISATIN HYDRAZONES AND THEIR ESTERS AS SHP2 INHIBITORS

CROSS REFERENCE TO RELATED APPLICATIONS

This application is a continuation of prior filed International Application, Serial Number PCT/US2010/031506 filed Apr. 16, 2010, which claims priority to U.S. provisional patent application No. 61/170,354 filed Apr. 17, 2009 which is hereby incorporated by reference into this disclosure.

STATEMENT OF GOVERNMENT INTEREST

This invention was made with Government support under Grant Nos. CA118210 and CA077467, awarded by the National Institutes of Health. The Government has certain rights in the invention.

FIELD OF INVENTION

This invention relates to cancer therapy. More specifically, this invention comprises novel Shp2 inhibitors, a method to develop new Shp2 inhibitors, and a method of treating cancer using the inhibitors.

BACKGROUND OF THE INVENTION

Tyrosyl phosphorylation regulates human cellular processes from cell differentiation and growth to apoptosis. The process of tyrosyl phosphorylation is regulated by protein-tyrosine phosphatases (PTP) and protein-tyrosine kinases (PTK). When this regulation is disrupted, diseases such as cancer can arise. (Mohi and Neel, The role of Shp2 (PTPN11) in cancer. Curr Opin Genet & Dev. 2007, 17, 23-30). Many studies in the last three decades have demonstrated the roles of various protein tyrosine kinases (PTKs) in human cancer (Blume-Jensen and Hunter, Oncogenic kinase signalling. Nature 2001; 411:355-65). PTK inhibitors such as imatinib and gefitinib are now well-recognized as targeted therapy drugs in cancer treatment (Deininger, et al., The development of imatinib as a therapeutic agent for chronic myeloid leukemia. Blood 2005; 105:2640-53; Mulloy, et al., Epidermal growth factor receptor mutants from human lung cancers exhibit enhanced catalytic activity and increased sensitivity to gefitinib. Cancer Res 2007; 67:2325-30). Though more research exists for PTKs, as the first PTK was synthesized 10 years earlier than the first PTP, recent discoveries have found that PTPs have a prominent role in tyrosyl phosphorylation. (Alonso, et al., Protein tyrosine phophatases in the human genome. Cell. 2004, 117, 699-711).

PTPs catalyze the reverse reaction of PTKs, however increasing evidence suggests that cell signaling and oncogenesis require coordinated action of both PTKs and PTPs. For instance, PTPs such as Shp2, PTP1B, Cdc25, and PRL-3 have been found to be positively involved in oncogenesis and tumor progression (Bentires-Alj, et al., Activating mutations of the noonan syndrome-associated SHP2/PTPN11 gene in human solid tumors and adult acute myelogenous leukemia. Cancer Res 2004; 64:8816-20; Boutros, et al., CDC25 phosphatases in cancer cells: key players? Good targets? Nat Rev Cancer 2007; 7:495-507; Stephens B J, Han H, Gokhale V, Von Hoff D D. PRL phosphatases as potential molecular targets in cancer. Mol Cancer Ther 2005; 4:1653-61; Tonks and Muthuswamy, A brake becomes an accelerator: PTP1B-a new therapeutic target for breast cancer. Cancer Cell 2007; 11:214-6). Consequently, the search for PTP inhibitors as a new class of potential drugs for targeted cancer therapy has intensified in recent years (Jiang and Zhang, Targeting PTPs with small molecule inhibitors in cancer treatment. Cancer Metastasis Rev 2008; 27:263-72; Lawrence, et al., Inhibitors of Src homology-2 domain containing protein tyrosine phosphatase-2 (Shp2) based on oxindole scaffolds. J Med Chem 2008; 51:4948-56; Hellmuth, et al., Specific inhibitors of the protein tyrosine phosphatase Shp2 identified by high-throughput docking. Proc Natl Acad Sci USA 2008; 105: 7275-80; Geronikaki, et al. 2-Thiazolylimino/heteroarylimino-5-arylidene-4-thiazolidinones as new agents with SHP-2 inhibitory action. J Med Chem 2008; 51:5221-8; Johnston, et al., Cdc25B dualspecificity phosphatase inhibitors identified in a high-throughput screen of the NIH compound library. Assay Drug Dev Technol 2009; 7:250-65).

Shp2, encoded by the PTPN11 gene, is a non-receptor PTP containing two SH2 domains, a PTP domain, and a C-terminal region (Neel, et al., The 'Shp'ing news: SH2 domain-containing tyrosine phosphatases in cell signaling. Trends Biochem Sci 2003; 28:284-93). It is part of the src homology domain (SH2) and necessary for embryonic development and growth factor, cytokine, and extra-cellular matrix signaling (Salmond and Alexander, SHP2 forecast for the immune system:fog gradually clearing. Trends Immunol 2006, 27, 154-60) and effect cell proliferation, differentiation, and migration. The N-SH2 domain in the wildtype Shp2 interacts with the PTP domain, resulting in autoinhibition of the Shp2 PTP activity. When the SH2 domains bind to specific phosphotyrosine docking sites in growth factor- or cytokine-stimulated cells, it relieves the autoinhibition and Shp2 is activated (Cunnick, et al., Phosphotyrosines 627 and 659 of Gab1 constitute a bisphosphoryl tyrosine-based activation motif (BTAM) conferring binding and activation of SHP2. J Biol Chem 2001; 276:24380-7).

A well-recognized Shp2-regulated signaling pathway is the Ras-Erk1/2 MAP pathway. For instance, Shp2 is positively involved in epidermal growth factor (EGF)-stimulated Erk1/2 activation (Cunnick, et al., Phosphotyrosines 627 and 659 of Gab1 constitute a bisphosphoryl tyrosine-based activation motif (BTAM) conferring inding and activation of SHP2. J Biol Chem 2001; 276:24380-7; Ren, et al., Roles of Gab1 and SHP2 in paxillin tyrosine dephosphorylation and Src activation in response to epidermal growth factor. J Biol Chem 2004; 279:8497-505). Shp2 PTP activity is required for transformation of human glioblastoma cells by EGFRvIII (Zhan, et al., The protein tyrosine phosphatase SHP-2 is required for EGFRvIII oncogenic transformation in human glioblastoma cells. Exp Cell Res 2009; 315:2343-57) and human mammary epithelial cells by ErbB2 (Zhou and Agazie, Molecular mechanism for SHP2 in promoting HER2-induced signaling and transformation. J Biol Chem 2009; 284:12226-34). In the last few years, mutations in the Shp2 gene PTPN11 have been identified in several types of leukemias and in some cases of solid tumors (Bentires-Alj, et al. Activating mutations of the noonan syndrome-associated SHP2/PTPN11 gene in human solid tumors and adult acute myelogenous leukemia. Cancer Res 2004; 64:8816-20; Tartaglia and Gelb, Germ-line and somatic PTPN11 mutations in human disease. Eur J Med Genet 2005; 48:81-96; Mohi and Neel, The role of Shp2 (PTPN11) in cancer. Curr Opin Genet & Dev. 2007, 17, 23-30).

Mutations in the PTPN11 gene and Shp2 can cause Noonan syndrome, juvenile myelomonocytic leukemia, acute myelogenous leukemia, and LEOPARD (lentigines, electrocardiogram abnormalities, ocular hypertelorism, pulmonic valvular stenosis, abnormalities of genitalia, retardation of growth, and deafness). Within these diseases, Shp2 is uninhibited and interacts with the docking protein Gab family. This interaction activates a pathway leading to cell proliferation and tumorigenesis. The identification of Shp2's role in these diseases is very important for developing cancer therapy. Targeting and inhibiting Shp2 with small molecule inhibitors has become a major goal in developing a new cancer therapy. These mutations and other cancer-associated Shp2 mutants are predicted or have been demonstrated to be gain-of-function mutations (Bentires-Alj, et al. Activating mutations of the noonan syndrome-associated SHP2/PTPN11 gene in human solid tumors and adult acute myelogenous leukemia. Cancer Res 2004; 64:8816-20; Ren, et al., Shp2E76K mutant confers cytokine-independent survival of TF-1 myeloid cells by up-regulating Bcl-XL. J Biol Chem 2007; 282:36463-73; Keilhack, et al., Diverse biochemical properties of Shp2 mutants. Implications for disease phenotypes. J Biol Chem 2005; 280:30984-93). Importantly, no loss-of-function Shp2 mutant has ever been found in human cancer.

Shp2 plays a positive role in the Ras-Erk1/2 MAP kinase pathway, however several reports indicated that Shp2 is a negative regulator of interferon (IFN) signaling. Shp2 was able to dephosphorylate STAT1 in vitro, suggesting that STAT1 is a substrate of Shp2 PTP (Wu, et al., SHP-2 is a dualspecificity phosphatase involved in Stat1 dephosphorylation at both tyrosine and serine residues in nuclei. J Biol Chem 2002; 277:47572-80). Consistently, increased IFN-stimulated STAT1 tyrosine phosphorylation was observed in mouse embryonic fibroblast cells lacking a functional Shp2 (Wu, et al., SHP-2 is a dualspecificity phosphatase involved in Stat1 dephosphorylation at both tyrosine and serine residues in nuclei. J Biol Chem 2002; 277:47572-80; You, et al., Shp-2 tyrosine phosphatase functions as a negative regulator of the interferon-stimulated Jak/STAT pathway. Mol Cell Biol 1999; 19:2416-24). The inhibitory effect of Shp2 on STAT1 tyrosine phosphorylation may contribute to modulation of the antiviral effect of IFN (Baron and Davignon, Inhibition of IFN-gamma-induced STAT1 tyrosine phosphorylation by human CMV is mediated by SHP2. J Immunol 2008; 181: 5530-6).

While PTPs have increasingly attracted attention as novel targets of cancer drug discovery, only a few selective PTP inhibitors have been characterized biologically. Among PTP inhibitors identified in recent years, many of them contain one or more negatively-charged functional groups (Jiang and Zhang, Targeting PTPs with small molecule inhibitors in cancer treatment. Cancer Metastasis Rev 2008; 27:263-72; Hellmuth, et al., Specific inhibitors of the protein tyrosine phosphatase Shp2 identified by high-throughput docking. Proc Natl Acad Sci USA 2008; 105:7275-80; Bialy and Waldmann, Inhibitors of protein tyrosine phosphatases: next-generation drugs? Angew Chem Int Ed Engl 2005; 44:3814-39; Chen, et al., Discovery of a novel shp2 protein tyrosine phosphatase inhibitor. Mol Pharmacol 2006; 70:562-70). This property is reminiscent of PTP substrates since phosphotyrosine is negatively charged and negatively charged Asp and Glu residues are frequently present near tyrosine phosphorylation sites. While aryl sulfonic compounds have been found to exert cellular activities in some cases (Hellmuth, et al., Specific inhibitors of the protein tyrosine phosphatase Shp2 identified by high-throughput docking. Proc Natl Acad Sci USA 2008; 105:7275-80; Zhan, et al. The protein tyrosine phosphatase SHP-2 is required for EGFRvIII oncogenic transformation in human glioblastoma cells. Exp Cell Res 2009; 315:2343-57; Chen, et al., Discovery of a novel shp2 protein tyrosine phosphatase inhibitor. Mol Pharmacol 2006; 70:562-70; Zhao, et al., Regulation of ACh receptor clustering by the tyrosine phosphatase Shp2. Dev Neurobiol 2007; 67:1789-801; Fuchikawa, et al. Protein tyrosine phosphatase SHP2 is involved in Semaphorin 4D-induced axon repulsion. Biochem Biophys Res Commun 2009; 385:6-10), compounds containing aryl phosphate or carboxylate groups often require modifications for cell permeation and/or pro-drug strategies for delivery into cells (Boutselis, e tal. Synthesis and cell-based activity of a potent and selective protein tyrosine phosphatase 1B inhibitor prodrug. J Med Chem 2007; 50:856-64).

Currently, there are a few known inhibitors of Shp2. Two of these compounds are CDL 4340-0580 and NAT6-297775, seen in FIG. 1. (Noren-Muller A., et al.: Discovery of protein phosphatase inhibitor classes by biology-oriented synthesis. Proc Natl Acad Sci USA. 2006, 103, 10606-11). Although these compounds have the ability to inhibit Shp2, they also inhibit tumor suppressor Shp1, which is not the cause of these malignancies. Ultimately, a Shp2 inhibitor should only affect Shp2 and not other important cellular processes.

Accordingly, there remains an unmet need for additional inhibitory compounds for the prevention and treatment of precancerous or cancerous lesions, particularly for lesions utilizing Shp2. The present invention further meets these important needs, and others, as will become apparent in the teachings that follow.

SUMMARY OF INVENTION

The development of a Shp2-specific inhibitor that does not cross-inhibit Shp1 is important for development of effective treatment modalities. Developing a Shp2-specific inhibitor is complicated by the similarity between Shp1 and Shp2, which share 60% overall sequence identity and approximately 75% similarity in their PTP domains. However, Shp1 and Shp2 catalytic domains have different substrate specificity (Tenev, T., et al., *J. Biol. Chem.* 1997, 272, 5966-73; O'Reilly, A., Neel, B., *Mol. Cell Biol.* 1998, 18, 161-77) suggesting that the catalytic cleft is not identical. Furthermore, the surface electrostatic potential of the catalytic cleft is much more positive in human Shp2 than in human Shp1. (Yang, J., et al., *J. Biol. Chem.* 1998, 273, 28199-207). The PTP catalytic cleft consists of a base and four sides in the 3D structures (Hof P, et al. *Cell* 1998, 92(4):441-450; Yang J, et al. *J. Biol. Chem.* 2003, 278(8):6516-6520). Although amino acid residues present at the base of Shp1 and Shp2 PTP catalytic clefts are identical, all four sides of the catalytic cleft contain one or more residues that are different between Shp1 and Shp2.

A previous study identified NSC-117199 as a lead compound of Shp2 inhibitor, and over 100 analogs synthesized (Lawrence, et al., Inhibitors of Src homology-2 domain containing protein tyrosine phosphatase-2 (Shp2) based on oxindole scaffolds. J Med Chem 2008; 51:4948-56). Based on the high throughput screening, XW2-011B from HePTP screens, seen in FIG. 2, was synthesized, exhibiting an $IC_{50}$ of 47.8 µM. Focused libraries based on these hits have been prepared and assessed for Shp2 inhibitory activity. As an initial step, building block molecules were synthesized. An indoline skeleton molecule was then constructed, which was used to couple with the individual building blocks to afford the target molecules. Additional target molecules were also produced by coupling different acid chlorides and isocyanates with the indoline core. Finally, a chemical probe was also synthesized as a subunit for potential small molecules to develop another biologically active, small molecule skeleton like the indoline. Novel alternative compounds for inhibiting a protein tyrosine phosphatase were generated having the general formula:

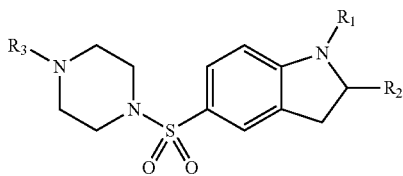

The indole $R_1$ is a functional group, which may be $CO(CH_2)_2CO_2H$, $COCH_2CH(OH)CO_2H$, $CO(CH)_2CO_2H$, $CONH(C_6H_4)Cl$, $CONH(C_6R_4)CH(CH_3)_2$, $CONH(C_6H_4)(Cl)_2$, $CO(CH_2)_3CO_2H$, $CO(C_6H_4)OCH_3$, $CO(C_5H_8)$, $CO(C_6H_4)Cl$, $CONHCH_2CO_2H$, $COCH_2CH(CH_3)_2$, $CONHCH(CHCH_3CH_2CH_3)(CO_2H)$, $CONH(C_6H_4)OCH_3$, $CO(C_6H_3)(Cl)_2$, $COCH_2(C_6H_4)Cl$, $CO(CH_2)_2CO_2H$, $CONH(C_6H_4)F$, $CONHCH(CH_3)CO_2H$, $CO(C_3H_5)$, $CONHCH(CH_2CHCH_3CH_3)(CO_2CH_2CH_3)$, $CO(C_6H_5)$, $CONHCH(CHCH_3CH_3)(CO_2H)$, $COCH_2CH(OH)(CO_2^-)\cdot Na^+$, $CONHCH(CH_3)(CO_2CH_2CH_3)$, $CONH(C_6H_4)CF_3$, $COCO_2H$, $CO(CH_2)_2CH_3$, $CONH(CH_2)_2CO_2H$, $CONHCH(CHCH_3CH_3)(CO_2CH_2CH_3)$, $CONHCH(CH_2CHCH_3CH_3)(CO_2H)$, $CONH(C_6H_5)$, $CONH(CH_2)_2CO_2CH_2CH_3$, $CONHCH(C_6H_5)(CO_2CH_2CH_3)$, $CONHCH(CHCH_3CH_3)(CO_2CH_3)$, $CONH(C_6H_4)CO_2H$, $CO(C_6H_8)CO_2H$, $CONHCH(CH_2C_6H_5)(CO_2H)$, $CONH(C_6H_4)CO_2CH_3$, $COCH_2OCH_3$, $COCH_2(C_6H_5)$, $COCF_3$, $CONHCH(CH_2CH_2CO_2H)(CO_2H)$, or $CONHCH_2CO_2CH_2CH_3$. The indole $R_2$ may be H, or $CH_3$; and the $R_3C_6H_4$—Cl, $C_6H_4$—$CO_2H$, $C_6H_4$—$CH_3$, $C_6H_4$—$(Cl)_2$, $C_6H_4$—$(CF_3)_2$, $C_6H_4$—$OCH_3$, $C_6H_4$—F, $C_6H_3$—$(Cl)(CH_3)$, or $C_6H_5$. The invention also provides for treating neoproliferative disease in an animal using the disclosed compound.

In addition, testing of SPI-112 (Compound 10m in Lawrence, et al., Inhibitors of Src homology-2 domain containing protein tyrosine phosphatase-2 (Shp2) based on oxindole scaffolds. J Med Chem 2008; 51:4948-56), among the best Shp2 inhibitor derived from NSC-117199, have shown that this Shp2 PTP inhibitor have low or poor in vivo activity. The studies show that these Shp2 PTP inhibitors have either a polar —$NO_2$ or a negatively charged —COOH group and have no detectable cellular activity, suggesting that they are not cell permeable. In the present invention, novel alternative compounds for inhibiting a protein tyrosine phosphatase were generated having the general formula:

a.

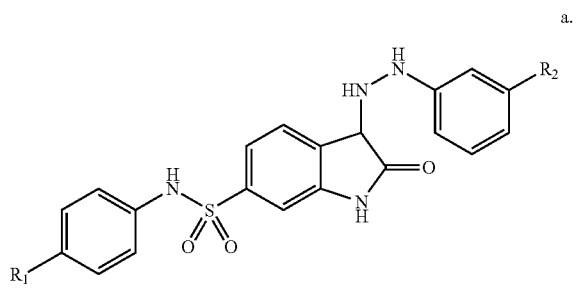

The $R_1$ moiety is F and $R_1$ moiety $COOCH_3$ and the meglumine salt $CO_2^-\cdot N^+H_2(CH_3)(CH_2CHOH)_4CH_2OH)$. A method of treating a neoproliferative disease using the described compound is also disclosed. In some embodiments, the above-disclosed compound is used with IFN-γ as a combined treatment. IFN-γ may be added sequentially or in combination with the compound.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

Figure 1:
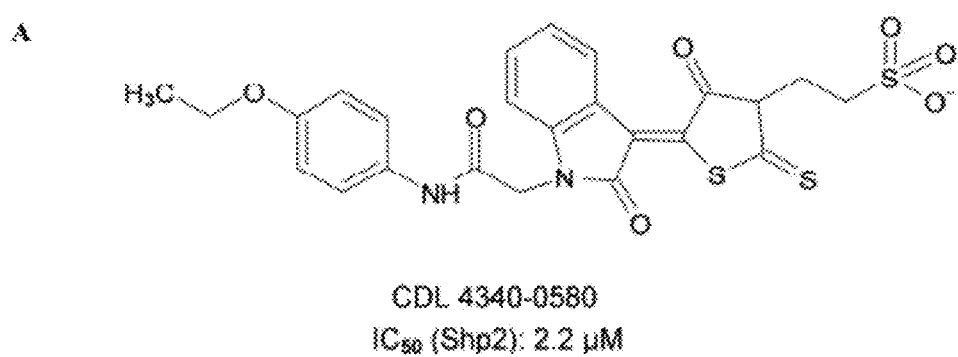
FIGS. 1(A) and (B) are diagrams of non-selective inhibitors of Shp2.
Figure 1:
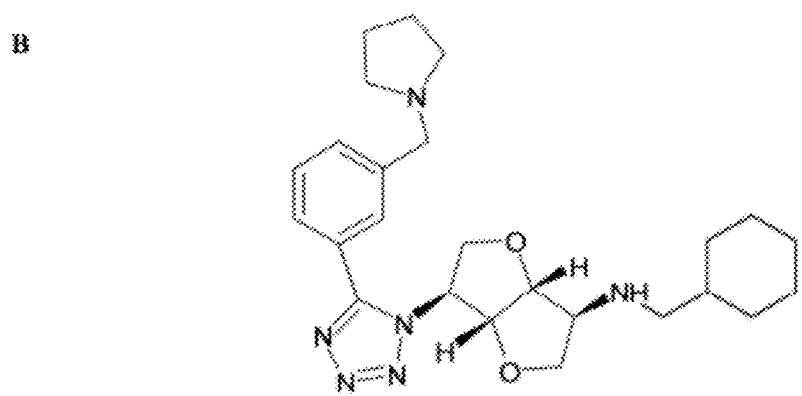
Figure 2:
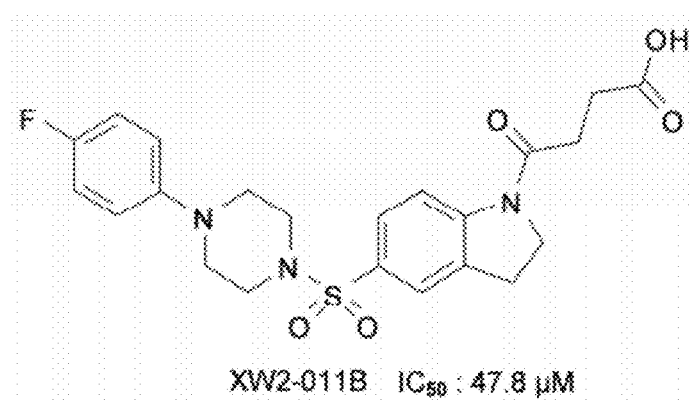
FIG. 2 is a Shp2 inhibitor identified through high throughput screening.

As used herein, the term "precancerous" refers to cells or tissues that have characteristics relating to changes that may lead to malignancy or cancer, such as mutations controlling cell growth and proliferation. Examples include adenomatous growths in breast and prostate tissue, or for example, conditions of dysplastic nevus syndromes, polyposis syndromes, prostatic dysplasia, and other neoplasms, whether clinically identifiable or not.

As used herein, "neoproliferative disease" mean a neoplasm, cancer, or precancerous lesion. The neoplasm or cancer may be benign or malignant.

As used herein, "patient" and "subject" are used interchangeable to mean humans, nonhuman primates, dogs, cats, sheep, goats, horses, cows, pigs and rodents. In particular, the "subjects" of the present invention are organisms in need of diagnosis or treatment for a cancer or pre-cancer or lesion thereof.

The pharmaceutical compositions of the subject invention can be formulated according to known methods for preparing pharmaceutically useful compositions. Furthermore, as used herein, the phrase "pharmaceutically acceptable carrier" means any of the standard pharmaceutically acceptable carriers. The pharmaceutically acceptable carrier can include diluents, adjuvants, and vehicles, as well as implant carriers, and inert, non-toxic solid or liquid fillers, diluents, or encapsulating material that does not react with the active ingredients of the invention. Examples include, but are not limited to, phosphate buffered saline, physiological saline, water, and emulsions, such as oil/water emulsions. The carrier can be a solvent or dispersing medium containing, for example, ethanol, polyol (for example, glycerol, propylene glycol, liquid polyethylene glycol, and the like), suitable mixtures thereof, and vegetable oils. Formulations are described in a number of sources that are well known and readily available to those skilled in the art. For example, *Remington's Pharmaceutical Sciences* (Martin E W [1995] Easton Pa., Mack Publishing Company, 19$^{th}$ ed.) describes formulations which can be used in connection with the subject invention.

Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question. The pharmaceutical composition can be adapted for various forms of administration. Administration can be continuous or at distinct intervals as can be determined by a person skilled in the art.

The "therapeutically effective amount" for purposes herein is thus determined by such considerations as are known in the art. A therapeutically effective amount of the compounds, or any combination thereof is that amount of active compound or pharmaceutical agent that elicits the biological or medicinal response in a tissue, system, animal or human that is being sought by a researcher, veterinarian, medical doctor or other clinician. The amount of Shp2 inhibitors, compounds described herein, or any combination thereof must be effective to achieve a response, including but not limited to total prevention of (e.g., protection against) and to improved survival rate or more rapid recovery, or improvement or elimination of symptoms associated with neoproliferative disease, including but not limited to, cancer and precancerous lesions, or other indicators as are selected as appropriate measures by those skilled in the art. In accordance with the present invention, a suitable single dose size is a dose that is capable of preventing or alleviating (reducing or eliminating) a symptom in a patient when administered one or more times over a suitable time period. One of skill in the art can readily determine appropriate single dose sizes for systemic administration based on the size of a mammal and the route of administration. An effective amount can be administered in one or more doses. In the case of cancer, the effective amount of the drug or composition may: (i) reduce the number of cancer cells; (ii) reduce tumor size; (iii) inhibit, retard, slow to some extent and preferably stop cancer cell infiltration into peripheral organs; (iv) inhibit (i.e., slow to some extent and preferably stop) tumor metastasis; (v) inhibit tumor growth; (vi) prevent or delay occurrence and/or recurrence of tumor; and/or (vii) relieve to some extent one or more of the symptoms associated with the cancer.

All reactions were monitored by thin layer chromatography (TLC) or $^1$H NMR. Some products, which could not be purified by simply washing, were purified by Flashmaster chromatography. All compounds were confirmed by $^1$H and $^{13}$C NMR, and Mass Spectra collected where available. After the purity and structure were confirmed, samples were tested for $IC_{50}$ by DiFMUP assay, seen in Table 1, appended.

Computer docking was performed with the X-ray crystal structure of human Shp2 (PDB identification code: 2SHP) (Hof, et al., Crystal structure of the tyrosine phosphatase SHP-2. Cell 1998; 92:441-50) using the GLIDE (Grid-Based Ligand Docking from Energetics software available from Schrödinger, L.L.C.) program similar to that reported (Chen, et al., Discovery of a novel shp2 protein tyrosine phosphatase inhibitor. Mol Pharmacol 2006; 70:562-70). The Jorgensen OPLS-2001 force field was applied in the GLIDE program. The optimal binding geometry was obtained by utilization of Monte Carlo sampling techniques coupled with energy minimization.

An anti-His-tag antibody (Qiagen) was immobilized on a CM5 Sensor Chip for Biacore T100 using a protocol similar to that described (Muller, et al., Tandem immobilized metal-ion affinity chromatography/immunoaffinity purification of His-tagged proteins—evaluation of two anti-His-tag monoclonal antibodies. Anal Biochem 1998; 259:54-61). His-tagged Shp2 (amino acids 1-525) was captured on this antibody surface for each cycle of compound or running buffer injection. SPI-112 meglumine salt was diluted in the running buffer (50 mM Bis-Tris HCl pH 7.0, 150 mM NaCl, 2 mM DTT, 0.01% TritonX-100, 3% DMSO) to yield final inhibitor concentrations of 10.2, 3.3, 1.1, 0.37, and 0.12 µM. Duplicate independent kinetics experiments were carried out in a manner similar to that used by Nordin and colleagues (Nordin, et al., Kinetic studies of small molecule interactions with protein kinases using biosensor technology. Anal Biochem 2005; 340:359-68). Kinetics analysis was performed using BIA evaluation software (GE Lifesciences, Little Chalfont, United Kingdom) fitting Langmuir (1:1) binding. Local $R_{max}$ calculations were used for our model fitting due to variation between cycles in theoretical $R_{max}$ values. Baseline RU drift over time in each experiment was corrected to improve the fitting (Joss L, et al., Interpreting kinetic rate constants from optical biosensor data recorded on a decaying surface. Anal Biochem 1998; 261:203-10).

The kinetic constant and rates of association and dissociation were from the average of two experiments.

MDA-MB-468 breast cancer cells and HT-29 colon cancer cells were from American Type Culture Collection (ATCC, Manassas, Va.) and maintained in Dulbecco's modified Eagle's medium (DMEM)/10% fetal bovine serum (FBS) and RPMI 1640/10% FBS, respectively. TF-1/Shp2E76K and TF-1/V cells were established by infection of TF-1 cells with a retrovirus encoding a Flag-tagged Shp2E76K mutant or the control virus as reported previously (Ren, et al., Shp2E76K mutant confers cytokine-independent survival of TF-1 myeloid cells by up-regulating Bcl-XL. J Biol Chem 2007; 282:36463-73). Flp-In-T-Rex-293 cells (Invitrogen, Carlsbad, Calif.) containing a doxycycline (dox)-inducible Gab1PH-Shp2ΔN chimera (Chen, et al., Discovery of a novel shp2 protein tyrosine phosphatase inhibitor. Mol Pharmacol 2006; 70:562-70) was used.

In vitro Shp2 PTP activity inhibition assay for determination of $IC_{50}$ was performed with a recombinant GST-Shp2 PTP domain protein using 6,8-difluoro-4-methylumbelliferyl phosphate (DiFMUP, Invitrogen) as the substrate similar to that described previously (Chen, et al., Discovery of a novel shp2 protein tyrosine phosphatase inhibitor. Mol Pharmacol 2006; 70:562-70). Curve fitting and $IC_{50}$ were obtained using the GraphPad Prism program (GraphPad Software).

Enzyme kinetics analysis was performed with a non-fusion Shp2 PTP protein in which the GST fragment had been removed by PreScission protease and using DiFMUP as the substrate. Reaction was carried out in duplicate at room temperature in black, half-area 96-well plates. Each reaction mixture (75 µl) contained 25 mM Hepes, pH 7.3, 50 mM NaCl, 1 mM dithiothreitol (DTT), 0.01% Triton-X100, 18.7-280 µM DiFMUP, 3% dimethyl sulfoxide (DMSO, vehicle) or SPI-112 (0.1, 0.25, 0.5, 1.0 µM), and 0.16 µM Shp2 PTP protein. Reaction was initiated by the addition of the enzyme. Fluorescent signal was measured at 5 and 10 min with a Wallac 1420 Victor² Multilabel Plate Reader (Perkin Elmer; Waltham, Mass.) at excitation/emission wavelengths of 355 nm/460 nm. Fluorescent signal was converted to the amount of product (nmole) using reference curve generated with 6,8-difluoro-4-methylumbelliferone (DiFMU, Invitrogen). Data obtained at the 5 min time point was used in the kinetics analysis. This is because >5% of substrate had been converted to the fluorescent DiFMU product at the later time point in some reaction wells and thus the steady state enzyme kinetics could no longer be ensured. Kinetics analysis of the data was performed with the VisualEnzymics program (Softymics).

To measure Shp2 PTP activity in immune complexes, cells were lysed in ice-cold PTP lysis buffer [25 mM Hepes, pH 7.4, 150 mM NaCl, 1 mM DTT, 2 mM EDTA, 0.5% Triton X-100, 1:50 diluted protease inhibitor cocktail (Roche, Basel, Switzerland)]. Cell lysate supernatants (0.2 mg/each) were incubated with an anti-Shp2 antibody (Santa Cruz Biotechnology, Santa Cruz, Calif.) or with an anti-Flag antibody M2 (Sigma-Aldrich, St. Louis, Mo.) plus protein G-Sepharose for 2 h at 4° C. Immunoprecipitates were washed twice with the PTP lysis buffer and twice with the Reaction Buffer A (25 mM Hepes, pH 7.4, 50 mM NaCl, 1 mM DTT, 0.05% Triton X-100). Each Shp2 immune complex was resuspended in 100 µl of reaction buffer containing 50 µM DiFMUP and incubated at room temperature for 20 min. After a brief centrifugation, supernatants were transferred into 96-well plates and the DiFMU fluorescence signal was measured. The remaining immune complex pellets were used for immunoblotting analysis of Shp2 protein.

For in vitro dephosphorylation of STAT1, STAT1 was immunoprecipitated from serum-starved HT-29 cells stimulated with IFN-γ (100 U/ml, 30 min). STAT1 immunoprecipitates were incubated with different amounts of GST-Shp2 PTP protein in Reaction Buffer A at 30° C. for 20 min. After the reaction, the immune complex was washed and analyzed by immunoblotting.

Cells ($6 \times 10^5$, TF-1/Shp2$^{E76K}$) were incubated in 12-well plates with indicated concentrations of SPI-112, SPI-112Me, or solvent (DMSO) for 5 h in 1 ml RPMI 1640/10% FBS at 37° C./5% $CO_2$. Aliquots of cell culture suspension (0.1 ml/each) were used for measuring the fluorescent signal in cell cultures. The remaining cell suspensions were centrifuged (3,000 rpm, 5 min). Cell pellets were washed 3 times with 1 ml culture medium. Each washed cell pellet was resuspended in 0.1 ml culture medium. Fluorescent signal in cell culture, cell-free medium, wash medium, and cell pellet was measured using an Envision 2102 Multilabel Reader (Perkin Elmer, Waltham, Mass.) at excitation/emission wavelengths of 485 nm/535 nm, and total fluorescent signal in each fraction was calculated. Values of fluorescent signal in cell-free supernatant and the wash solution were combined and designated as fluorescent signal in the cell-free medium.

Cells were treated as indicated in figure legends. Except experiments involving measurement of Shp2 PTP activity in immune complex, cells were lysed with the lysis buffer (50 mM Tris-HCl, pH 7.5, 150 mM NaCl, 1 mM EDTA, 1 mM EGTA, 25 mM NaF, 5 mM sodium pyrophosphate, 1 mM $Na_3VO_4$, 1 mM dithiothreitol, 20 mM p-nitrophenyl phosphate, 1% Triton X-100, 1:50 diluted protease inhibitor cocktail). After incubation on ice for 30 min, cell lysates were centrifuged twice at 16,000 rpm with a microfuge at 4° C. for 15 min. Cleared cell lysate supernatants were used for immunoblotting analysis or incubated with specific antibodies indicated in figure legends for immunoprecipitation. Immune complexes were collected with protein G-agarose or protein A-agarose. Immunoprecipitated proteins were separated on SDS-polyacrylamine gels and transferred to nitrocellulose membranes. Immunoblotting was performed as described previously (Ren, et al., Roles of Gab1 and SHP2 in paxillin tyrosine dephosphorylation and Src activation in response to epidermal growth factor. J Biol Chem 2004; 279:8497-505).

TF-1/Shp2$^{E76K}$ and HT-29 Cells (1,000 cells/well in triplicate) were plated in 96-well plates in RPMI160/10% FBS plus test agent(s) in a total volume of 100 µl. The volume of SPI-112Me or SPI-112 was kept <0.1% of the total volume. After incubation for 4 days at 37° C./5% $CO_2$, relative viable cell number was measured using the CelltiterGlo reagent (Promega) following the supplier's instruction. Synergism of two agents was calculated based on the Bliss definition (Greco, et al., The search for cytotoxic synergy between anticancer agents: a case of Dorothy and the ruby slippers? J Natl Cancer Inst 1996; 88:699-700) as below:

Assume X is the fraction of inhibition caused by the first agent, Y is the fraction of inhibition caused by the second agent, and Z is the fraction of inhibition caused by the combination of both agents, If Z=X+Y−XY, then the effect of two agents is additive.
If Z>X+Y−XY, then the effect of two agents is synergistic.
If Z<X+Y−XY, then the effect of two agents is antagonistic.

Apoptosis was examined using the ethidium bromide and acridine orange (EB/AO) staining assay (Ribble, et al., A simple technique for quantifying apoptosis in 96-well plates. BMC Biotechnol 2005; 5:12). Cells were incubated in granulocyte-macrophage colony-stimulating factor (GM-CSF)-free RPMI1640/10% FBS medium at 37° C./5% $CO_2$ in the presence of absence of SPI-112Me as indicated in the figure legend for 3 days. Aliquots (100 μl/each) of cells were then transferred to a 96-well plate and centrifuged at 1,000 rpm. EB/AO dye mix (100 μg/ml EB and 100 μg/ml AO in PBS) were added to each well (8 μl/well). Nuclear staining by EB/AO were examined under a fluorescent microscope (400× magnification, excitation filter: 480/30 nm; dichromatic mirror cut-on: 505 nm LP; barrier filter 535/40 nm). Live, apoptotic, and necrotic cells were enumerated in at least 150 cells in multiple fields in two wells. Data were from three independent experiments.

Cell migration assay was performed using polycarbonate membrane Transwell cell culture insert (6.5 mm, 8.0 μM pore size tissue culture treated, Costar). The membrane was coated with rat tail type I collagen (10 μg/ml) overnight at 4° C. and air-dried. MDA-MB-468 cells ($2.5 \times 10^4$) in 0.2 ml DMEM/0.1% BSA were placed in the upper chamber. The lower chamber contained 0.6 ml DMEM/1% FBS. EGF (10 ng/ml) was included in the media in both chambers where indicated. After incubation at 37° C./5% $CO_2$ for 16 h, cells on the upper membrane surface were removed with a cotton swab. Cells that had migrated to the lower side of membrane were fixed and stained using the HEMA3 reagents (Fisher Scientific, Waltham, Mass.). Cells were enumerated under a microscope in at least 8 randomly selected fields per well.

Luciferase reporter assays were conducted using HT-29 cells ($5 \times 10^5$ cells/each in 12-well plate) were co-transfected with 1.6 μg pISRE-Luc (Clontech, Mountain View, Calif.) and 0.4 μg β-gal plasmids with LipofectAMINE 2000 reagent. Eighteen hours after transfection, cells were incubated in fresh medium, pretreated with indicated concentrations of SPI-112Me or mocked treated for 2 h, and then stimulated with 50 U/ml IFN-γ for 6 h or left unstimulated. Luciferase and β-galactosidase activities were determined as described (Ren, et al., Shp2E76K mutant confers cytokine-independent survival of TF-1 myeloid cells by up-regulating Bcl-XL. J Biol Chem 2007; 282:36463-73). The luciferase activity was then normalized to β-galactosidase-galactosidase activity as an internal control for transfection efficiency.

EXAMPLE 1

Figure 3:
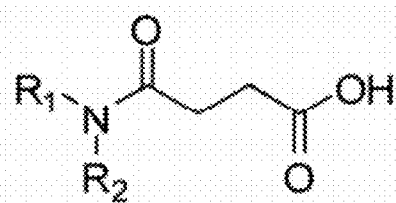
FIG. 3 is an image of an amide building block of the present invention.

To synthesize sulfonyl indulines of the invention, amide building blocks were first generated. Amine (5 mmol) was added drop-ise to a solution of succinic anhydride (0.5 g, 5 mmol) in anhydrous tetrahydrofuran (0.6 mL) at room temperature under argon, as seen in FIG. 3. After stirring overnight, the precipitate was collected by filtration and washed with EtOAc/hexane (1:2 by volume) to obtain crude product, which could be used directly for the next step, as described by Fuji, et al., (EP0470702 A1; 1992).

Indoline was synthesized by dissolving Indoline (12.6 mL, 0.11 mol) in dichloromethane (100 mL) at 0° C. Trifluoroacetic anhydride (29.5 mL, 0.21 mol) was added drop-wise over 1 hour. After stirring for another 1 hr, the reaction was quenched with water at 0° C. The mixture was extracted with dichloromethane, and the organic layer was washed with $NaHCO_3$ (sat. sol.) and brine. After concentration, the solid was washed with hexane to afford crude product JF013. Product JF013 (10.0 g, 46.5 mmol) was added to chlorosulfonic acid (15.46 mL, 233.0 mmol) drop-wise at 0° C. in 1 hour. After addition, the reaction was warmed to room temperature and then heated to 70° C. for 2.5 hours. After cooling down, the solid was filtered out and washed with water to afford crude product JF017.

To a solution of JF017 (10.8 g, 34.6 mmol) in dichloromethane (150 mL) was added piperizine (6.8 g, 34.6 mmol) and pyridine (5.8 mL, 69.2 mmol) at room temperature. After stirring over night, the mixture was concentrated. The solid was washed with water to afford JF018.

Figure 4:
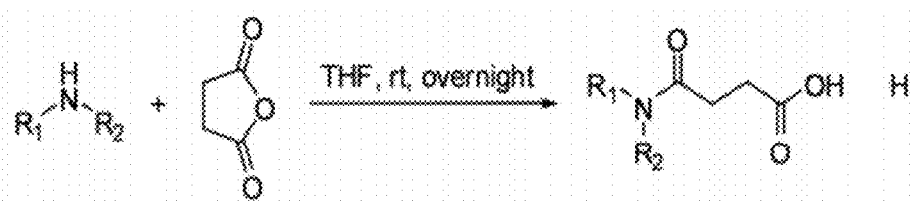
FIG. 4 is a chemical diagram of a reaction scheme for synthesizing the amide building blocks of the present invention.

To a solution of JF018 (16.36 g, 35.0 mmol) in tetrahydrofuran (90 mL) NaOH (1.0 M in $H_2O$, 11.5 mL) was added slowly, seen in FIG. 4. The reaction was stirred overnight. After concentration, the solid was washed with water to afford the indoline compound, JF019, (Borror A. L., et al.: Regioselectivity of electrophilic aromatic substitution: Syntheses of 6- and 7-Sulfamoylindolines and -indoles. J Org Chem. 1988, 46, 2047-2052; Fraley, et al.: Optimization of the indoyl quinolinone class of KDR (VEGFR-2) kinase inhibitors: effects of 5-amido- and 5-sulphonamido-indolyl groups on pharmocokinetics and hERG binding. Bioorg & Med Chem Letters. 2004, 14, 351-355), seen in FIG. 5.

Figure 6:
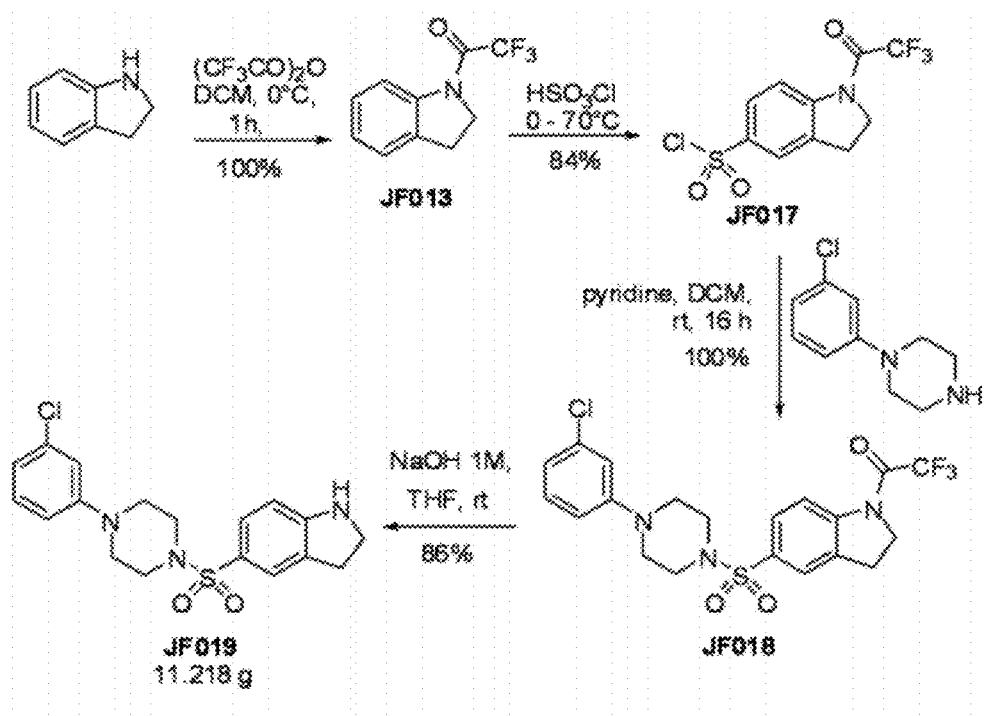
FIG. 6 is a chemical diagram of a reaction for synthesizing the indoline skeleton molecule of the present invention.
Figure 7:
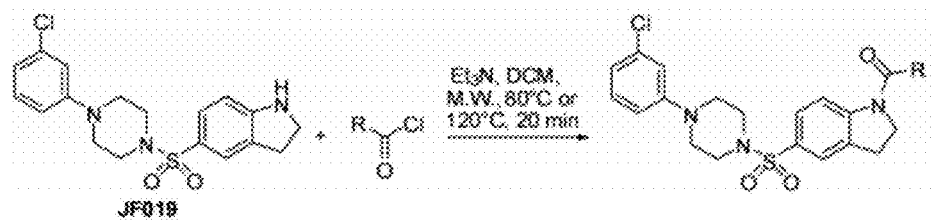
FIG. 7 is a chemical diagram of a reaction coupling an acid chloride to the indoline skeleton molecule of the present invention.

Indoline synthesis was scaled up, producing a large batch of inodline skeleton to act as scaffold for coupling the building blocks, as seen in FIG. 6. The indoline skeleton was then coupled with an acid chloride, as seen in FIG. 7. Triethylamine (16.94 μl, 0.13 mmol) and acid chloride (0.13 mmol) were added to a solution of JF019 (50.0 mg, 0.13 mmol) in dichloromethane (0.5 mL) at room temperature under argon was added. The reaction mixture was heated at 80 or 120° C. for 20 min in microwave. After concentration, the product was purified by washing with water, and ethyl acetate/hexane (3:7). In some particular cases, products were purified by chromatography.

Figure 8:
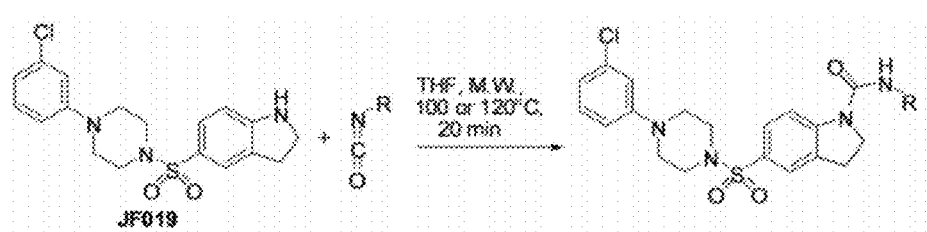
FIG. 8 is a chemical diagram of a reaction coupling an isocyanate to the indoline skeleton molecule of the present invention.

In alternative compounds, indoline was coupled with isocyanates, seen in FIG. 8. Isocyanate (0.13 mmol) was added to a solution of JF019 (50.0 mg, 0.13 mmol) in tetrahydrofuran (0.5 mL) at room temperature under argon, and the reaction mixture was heated to 100 or 120° C. in microwave for 20 min. After concentration, the product was triturated with water, filtered and washed with ethyl acetate/hexane mixture (3:7). In some instances, products were purified by chromatography.

Figure 9:
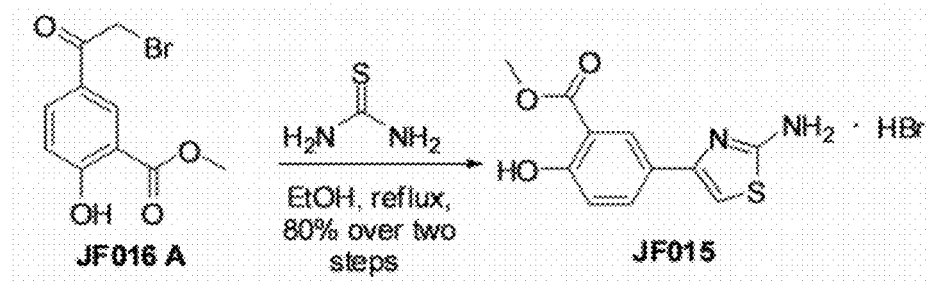
FIG. 9 is a chemical diagram of a reaction, based on chemical probe synthesis.

A chemical probe was synthesized by adding $Br_2$ (0.5 M in $CHCl_3$, 2.50 mmol, 5.00 mL) drop-wise at 0° C. to a solution of methyl 5-acetylsalicylate (485 mg, 2.50 mmol) and $AlCl_3$ (100 mg, 0.75 mmol) in $Et_2O$ (6.25 mL), seen in FIG. 9. After stirring at room temperature for 27 hours, the mixture was washed with $NaHCO_3$ (sat. sol.) and brine. The organic layer was separated, dried over $Na_2SO_4$ and concentrated to afford the bromide JF016A (593 mg). Then thiourea (16.7 mg, 0.22 mmol) was dissolved in EtOH (1.75 mL), followed by addition of JF016A (60 mg, 0.22 mmol). After stirring at room temperature for 2 hours, the reaction mixture was concentrated and recrystallized from MeOH/$Et_2O$ to afford the aminothiazole, JF015. (Goodwin, et al, Synthesis of $^{13}C$, $^2H_3$-Salmeterol: An analytical internal standard for pharmacokinetic studies. J Labelled Cpd. Radiopharm. 2000, 43, 65-75; Herschhorn, et al, De Novo parallel design, synthesis and evaluation of inhibitors against the reverse transcriptase of human immunodeficiency virus type-1 and drug-resistant variants. J Med Chem, 2007, 50, 2370-2384).

A few amide building blocks were prepared for the library synthesis of the indoline type of compounds. A variety of different building blocks were used to obtain small molecules of low IC$_{50}$, high specificity and good cell permeability. Normally, the reaction afforded the product as a solid after concentration. However, if the initial reaction produced sticky oil, ether was used to triturate solid out.

TABLE 2

The synthesized building blocks used in compounds formation. Compound yield are presented.

| Building Block | Yield (%) |
|---|---|
| JF001 (morpholine-succinic acid amide) | 36.6 |
| JF003 (4-(4-fluorophenyl)piperazine-succinic acid amide) | 93.0 |
| JF005 (N-cyclopropyl succinamic acid) | 22.1 |
| JF006 (N,N-dimethyl succinamic acid) | 61.1 |
| JF007 (piperidine succinamic acid) | 100.0 |
| JF010 (N-benzyl-N-methyl succinamic acid) | 100.0 |

JF007 and JF010 were produced in the highest yields and were the easiest building blocks to synthesize. The workup for these molecules only consisted of dissolving in water, acidifying, and extracting with ethyl acetate. The workup for JF003 was also simple, only requiring filtering and washing with ethyl acetate and hexane.

The Indoline skeleton was then synthesized. Indoline subunit synthesis was simple as the indoline was protected with trifluoroacetyl group, followed by the reaction with chlorosulfonic acid, seen in FIG. 9. The resulted sulfonyl chloride JF017 was coupled with piperizine to afford compound JF018. After deprotection under basic condition, the indoline core H019 was produced in high yield. The crude product of every step could be directly used in the successive step without purification.

Figure 10:
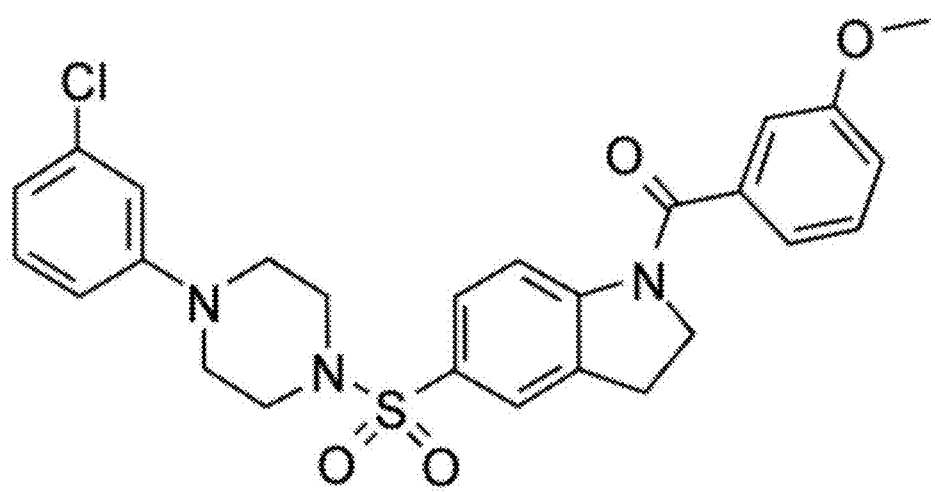
FIG. 10 is a diagram of an inhibitory molecule of the present invention using coupling of indoline to acid chlorides.

JHE-02-035A, seen in FIG. 10, shows a good IC$_{50}$ of 7.8 µM. To improve the potency, selectivity, and cell permeability, analogs bearing benzamide groups at the NH-terminus of the indoline were synthesized. The coupling reactions of indoline JF018 with acid chlorides were carried out under microwave conditions. Due to the strong electron-withdrawing sulfonyl group on the indoline ring, the reactions must be heated up to around 80° C. to around 100° C. based on the reactivity of the acid chlorides. All acid chlorides synthesized were fully analyzed by $^1$H and $^{13}$C NMR. Mass spectrometry was obtained, where available. JF020, JF021 and JF022 were tested for IC$_{50}$ determinations. The yields of all analogs synthesized are tabulated in Table 3.

TABLE 3

Percent yields and IC$_{50}$ results for synthesized compounds.

| Analog R Group | Yield (%) | IC$_{50}$ |
|---|---|---|
| JF022 (phenyl) | 86.9 | 8.4 ± 2.3 |
| JF021 (4-chlorophenyl) | 91.0 | 10.4 ± 2.0 |
| JF020 (3-chlorophenyl) | 92.2 | 5.7 ± 3.9 |
| JF023 (3,4-dichlorophenyl) | 27.3 | 7.1 ± 1.8 |
| JF024 (2,4-dichlorophenyl) | 77.3 | 7.6 ± 1.3 |

TABLE 3-continued

Percent yields and IC$_{50}$ results for synthesized compounds.

| Analog R Group | Yield (%) | IC$_{50}$ |
|---|---|---|
| 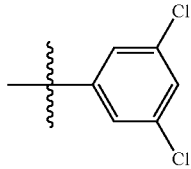 JF025 | 89.5 | 8.2 ± 2.6 |
| 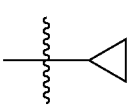 JF027 | 92.8 | 8.5 ± 2.0 |
| 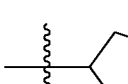 JF026 | 88.3 | 6.9 ± 2.2 |
| 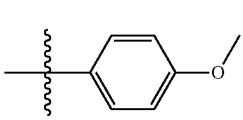 JF028 | 95.1 | 6.3 ± 2.9 |
| 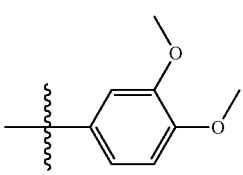 JF029 | 84.0 | ND |
| 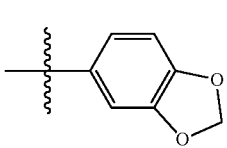 JF030 | 95.1 | ND |
| 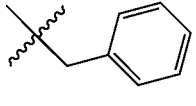 JF031 | 84.4 | 22.8 ± 4.5 |
| 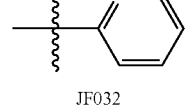 JF032 | 56.0 | ND |

The structural activity of the compounds was then examined. Compound JF022, without functional groups on the phenyl ring, was synthesized to determine whether a functional group is necessary to improve the biological activity. Compounds JF020 to JF021 were developed for examining the effect of a meta- or para-position chloride on a phenyl ring. To examine the effects of having two chlorides on the phenyl ring, JF023 features meta- and para-positions, JF024 features ortho- and para-positions, and JF025 features both meta-positions. Analogs with one chloride in the ortho-position and one analog with chlorides in both ortho-positions have also been synthesized.

F028, JF029, and JF030 are useful in determining the effects of methoxy groups on the phenyl ring. JF028 has the methoxy group on the para-position. Other possible compounds could contain a methoxy group on the meta- or ortho-positions. JF029 features two methoxy groups on the meta- and para-positions. These active groups are also attached to different positions of the phenyl ring to fully examine the effect of two methoxy groups on the phenyl ring. JF030 contains 1,3-dioxole group on the phenyl ring.

JF031 and JF032 are two different series of compounds that would provide starting points for further investigation. JF031 contains a benzyl group instead of the phenyl group to lengthen the linker. JF032 is a starting point to test the effect of a picolinoyl group on the molecule. Compounds JF026 and JF027, analogs with an aliphatic ring instead of phenyl ring, were also synthesized in high yields. Further, analogs with other rings, like cyclobutane, cyclohexane, and cycloheptane, were prepared.

Figure 11:
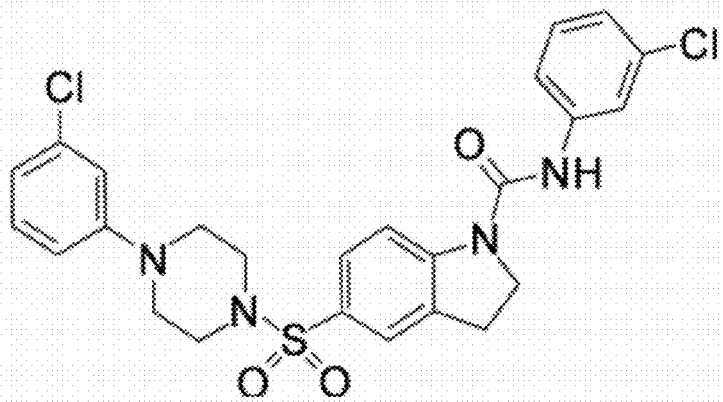
FIGS. 11(A) and (B) are diagrams of an inhibitory molecules of the present invention using coupling of isocyanate to the indoline skeleton molecule.
Figure 11:
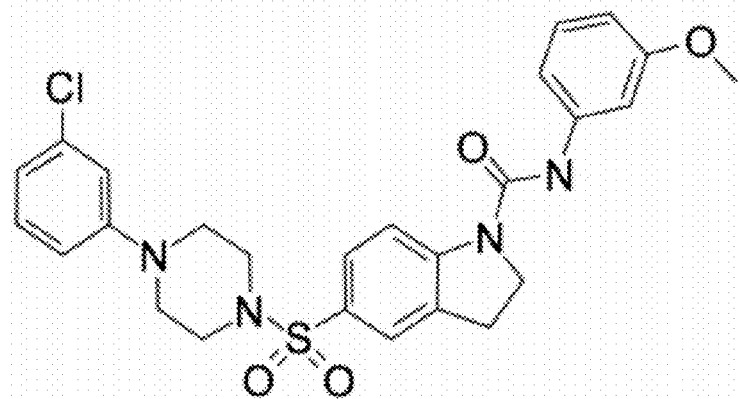

Compounds JHE-02-032A and JHE-02-032B, depicted in FIGS. 11(A) and (B), exhibit drug efficacy, measured by IC$_{50}$, of 2.4 μM and 4.8 μM respectively. To improve the IC$_{50}$, selectivity, and cell permeability, analogs with a urea group at the NH-terminus of the indoline were synthesized. The isocyanate analogs were more difficult to synthesize than the acid chloride analogs, and most of the compounds required a small excess of the isocyanates or higher microwave temperatures to fully react. Flashmaster chromatography was used to purify the products. The isocyanate analogs were fully analyzed by $^1$H and $^{13}$C NMR and percent yields tabulated, seen in Table 4.

TABLE 4

Percent yields and IC$_{50}$ results.

| Analog R Group | Yield (%) | IC$_{50}$ |
|---|---|---|
| 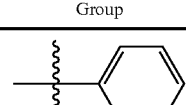 JF033 | 85.4 | 11.7 ± 1.4 |
| 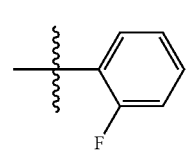 JF035 | 62.4 | 12.2 ± 2.0 |
| 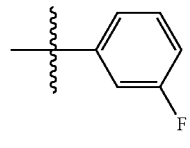 JF039 | 84.0 | 8.1 ± 1.7 |
| 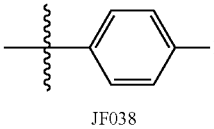 JF038 | 62.4 | 12.6 ± 5.4 |

TABLE 4-continued

Percent yields and IC$_{50}$ results.

| Analog R Group | Yield (%) | IC$_{50}$ |
|---|---|---|
| 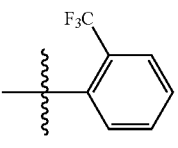 JF040 | 68.1 | 9.0 ± 1.7 |

F033 was the base compound with only a benzene ring. JF035, JF039, and JF038 have a fluorine at the ortho, meta, or para positions, respectively. The IC$_{50}$ data for these compounds are used to provide a comparison of the effect that fluorine has on the phenyl ring in different positions. JF040 is an analog that contains a trifluoromethyl group in the ortho position.

EXAMPLE 2

Chemical Synthesis of SPI-112 and SPI-112Me

Figure 12:
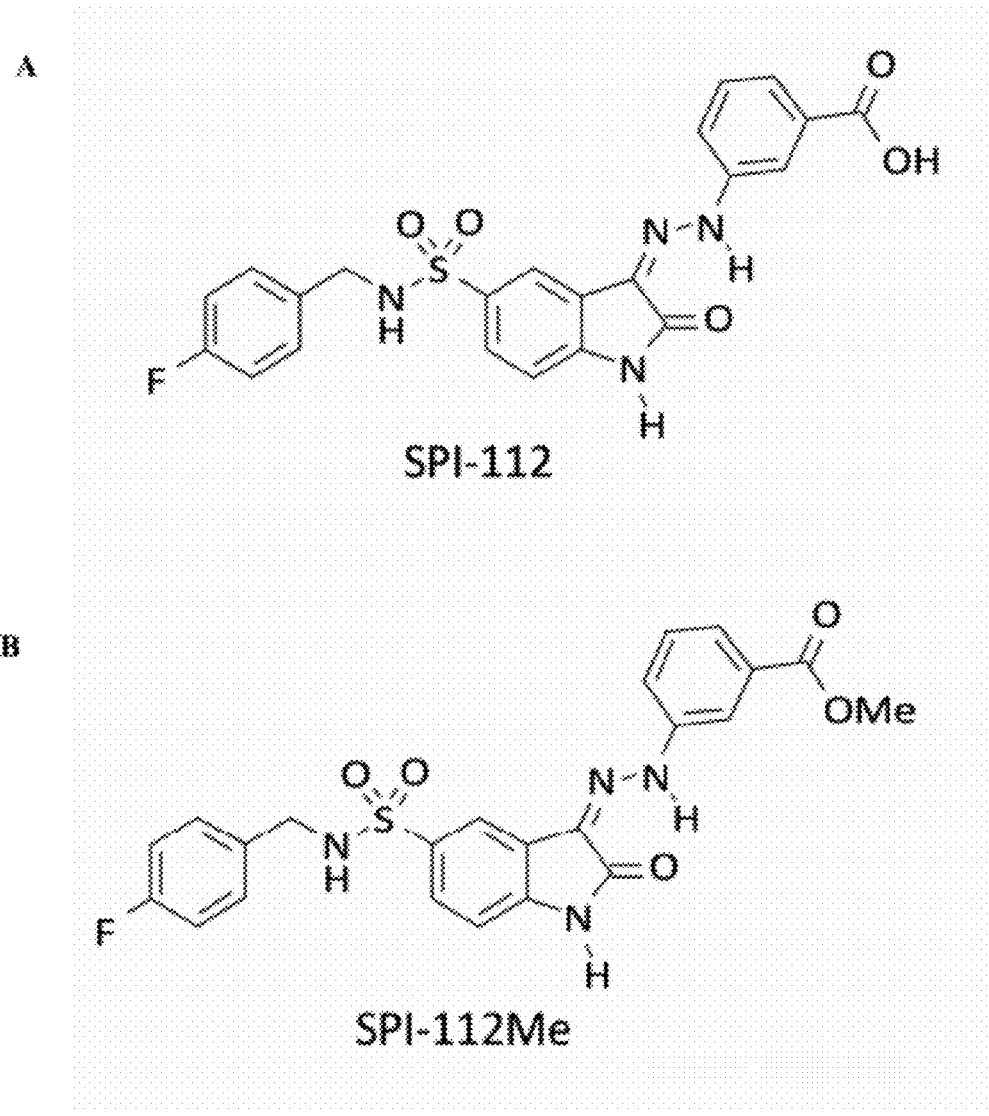
FIGS. 12(A) and (B) are diagrams showing (A) SPI-112 and its methyl ester prodrug (B) SPI-112Me.
Figure 13:
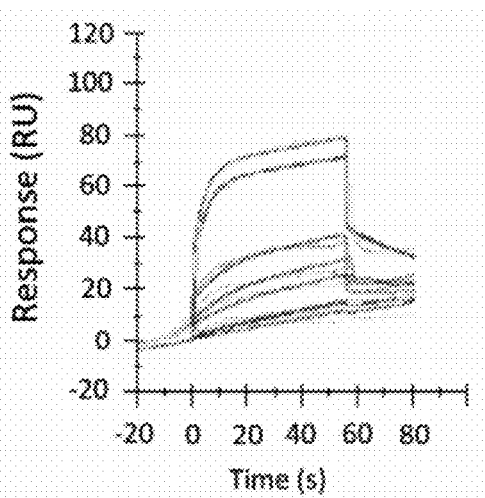
FIG. 13 is a Biacore sensorgram of SPI-112 binding to His-tagged Shp2 at the inhibitor concentrations of 10, 2, 3.3, 1.1, 0.37, and 0.12 µM. The data were locally fit to a 1:1 interaction model (black lines).

SPI-112, seen in FIG. 12(A), was synthesized based on a hit (NSC-117199) from the NCI Diversity Set-1 in our lead optimization effort (Lawrence, et al., Inhibitors of Src homology-2 domain containing protein tyrosine phosphatase-2 (Shp2) based on oxindole scaffolds. J Med Chem 2008; 51:4948-56). In SPR binding assay, SPI-112 displayed a 1:1 stoichiometric binding kinetics to Shp2 with a kinetic constant (K$_D$) of 1.30+0.14 μM and the association and dissociation rates of K$_a$=2.24×10$^4$/Ms and K$_d$=0.029/s, seen in FIG. 13. However, SPI-112 and other NSC-117199 analogs had no detectable activity in cell-based Shp2 inhibition assays, suggesting that they are not cell permeable. This is likely due to the presence of a negatively charged carboxylic acid on these Shp2 inhibitors.

Figure 5:
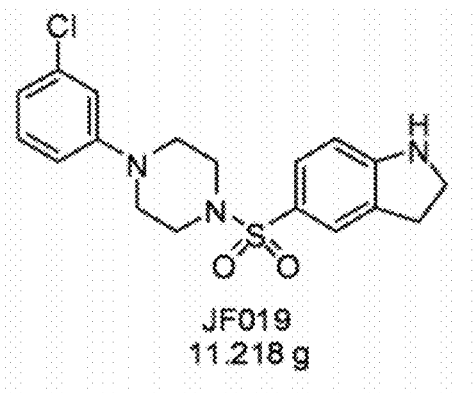
FIG. 5 is a diagram of the indoline skeleton molecule of the present invention.

SPI-112 [(Z)-3-(2-(5-(N-(4-fluorobenzyl)sulfamoyl)-2-oxoindolin-3-ylidene)hydrazinyl)benzoic acid] and SPI-112Me [(Z)-3-(2-(5-(N-(4-fluorobenzyl)sulfamoyl)-2-oxoindolin-3-ylidene) hydrazinyl)benzoic acid methyl ester] were synthesized using procedure similar to that described previously (Lawrence, et al., Inhibitors of Src homology-2 domain containing protein tyrosine phosphatase-2 (Shp2) based on oxindole scaffolds. J Med Chem 2008; 51:4948-56). Several libraries of hydrazones were prepared by combining a 5-substituted isatin with commercially available hydrazines; the sulfonyl and carboxyl groups were elaborated with a further set of amines to provide sulfonamides and amides, as described in Wu, et al. (PCT/US2009/042305; 2009). The novel oxindole hydrazone sulfonamide library was developed using commercially available building blocks as shown in FIG. 5 of Wu, et al. (PCT/US2009/042305; 2009). The oxindolesulfonyl chloride was obtained from commercially available isatin-5-sulfonic acid according to a literature reported procedure. (Lee, D., et al., J. Med. Chem. 2001, 44, 2015-2026). Isatin-5-sulfonyl chloride was coupled to a series of requisite amines to obtain the sulfonamide library. The hydrazone library was obtained by microwave assisted coupling of the crude sulfonamide library with an appropriate set of hydrazines in moderate yields.

To circumvent the cell permeation issue, a methyl ester analog of SPI-112 was prepared (SPI-112Me) to shield the negative charge of the carboxylic acid group of SPI-112, seen in FIG. 12(B). The methyl ester analog hydrolyzes to the corresponding carboxylic acid by cellular esterases upon entry into cells similar to other methyl ester prodrugs (Streiber, et al., Methyl esters of N-(dicyclohexyl)acetyl-piperidine-4-(benzylidene-4-carboxylic acids) as drugs and prodrugs: a new strategy for dual inhibition of 5 alpha-reductase type 1 and type 2. J Pharm Sci 2005; 94:473-80; Manne, et al., Bisubstrate inhibitors of farnesyltransferase: a novel class of specific inhibitors of ras transformed cells. Oncogene 1995; 10:1763-79).

Figure 14:
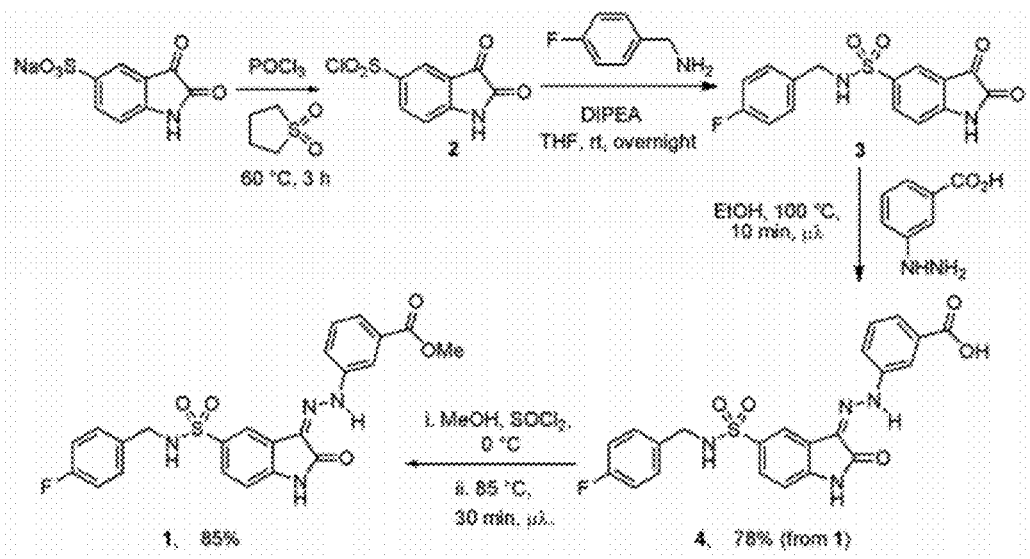
FIG. 14 is a chemical scheme for synthesizing the preparation of the benzyl oxindole ester 1 (SPI-112Me).

The methyl ester 1 (SPI-112Me), seen in FIG. 14, was prepared using the procedure similar to that described earlier (Lawrence, et al., Inhibitors of Src homology-2 domain containing protein tyrosine phosphatase-2 (Shpt) based on oxindole scaffolds. J Med Chem 2008; 51:4948-56).

2,3-Dioxoindoline-5-sulfonyl chloride 2 was generated using the procedure described by Lee et al. (Lee, et al. Potent and selective nonpeptide inhibitors of caspases 3 and 7. J Med Chem 2001; 44:2015-26) from isatin-5-sulfonic acid sodium salt dihydrate (Aldrich) (4.25 g) gave 2 (7.14 g, 40%). 2,3-Dioxo-2,3-dihydro-1H-indole-5-sulfonic acid 4-fluorobenzylamide 3. Diisopropylethylamine (DIPEA) (6.03 mL, 34.9 mmol) and 4-fluorobenzylamine (2.80 g, 22.35 mmol) were added to a solution of the sulfonyl chloride 2 (4.25 g, 17.25 mmol) in anhydrous THF (120 mL) at 0° C. under inert atmosphere. The reaction mixture was allowed to warm to room temperature and was stirred overnight. The resulting mixture was poured into water (100 mL) and extracted with ethyl acetate (3×50 mL). The combined extracts were dried (Na$_2$SO$_4$) and evaporated to provide 3 (7.14 g) as a yellow-orange solid. This crude product was used without further purification.

The sulfonamide 3 was prepared from the sulfonyl chloride 2 and used without purification. When the reaction of 3 was performed on a small scale (0.5 g), the product carboxylic acid was isolated as a single geometric isomer (previously assigned as the Z-isomer). Attempts to prepare the reaction at larger scales in the microwave reactor led to significant contamination of the product with the E-isomer).

(Z)-3-(2-(5-(N-(4-Fluorobenzyl)sulfamoyl)-2-oxoindolin-3-ylidene)hydrazinyl)benzoic acid 4 was then generated using a mixture of crude 3 (0.5 g) and 3-hydrazinobenzoic acid (0.23 g, 1.5 mmol) in ethanol (5.0 mL) were heated in a microwave reactor (Biotage Initiator) for 10 minutes at 100° C. The yellow solid that formed was isolated by filtration on a sintered funnel to provide the product (0.44 g). Under these optimized reaction conditions, approximately 3% of the E isomer was observed by $^1$H NMR. The process was repeated 3 times with the same amounts (exceeding the indicated amounts led to product contaminated with 10% of the E isomer), as seen in FIG. 14. The combined yield of 4 was 1.77 g (78% from 2). The analytical data of 4 ($^1$H NMR, $^{13}$C NMR, LC-MS) agrees with that previously reported (Lawrence, et al., Inhibitors of Src homology-2 domain containing protein tyrosine phosphatase-2 (Shp2) based on oxindole scaffolds. J Med Chem 2008; 51:4948-56)

Figure 15:
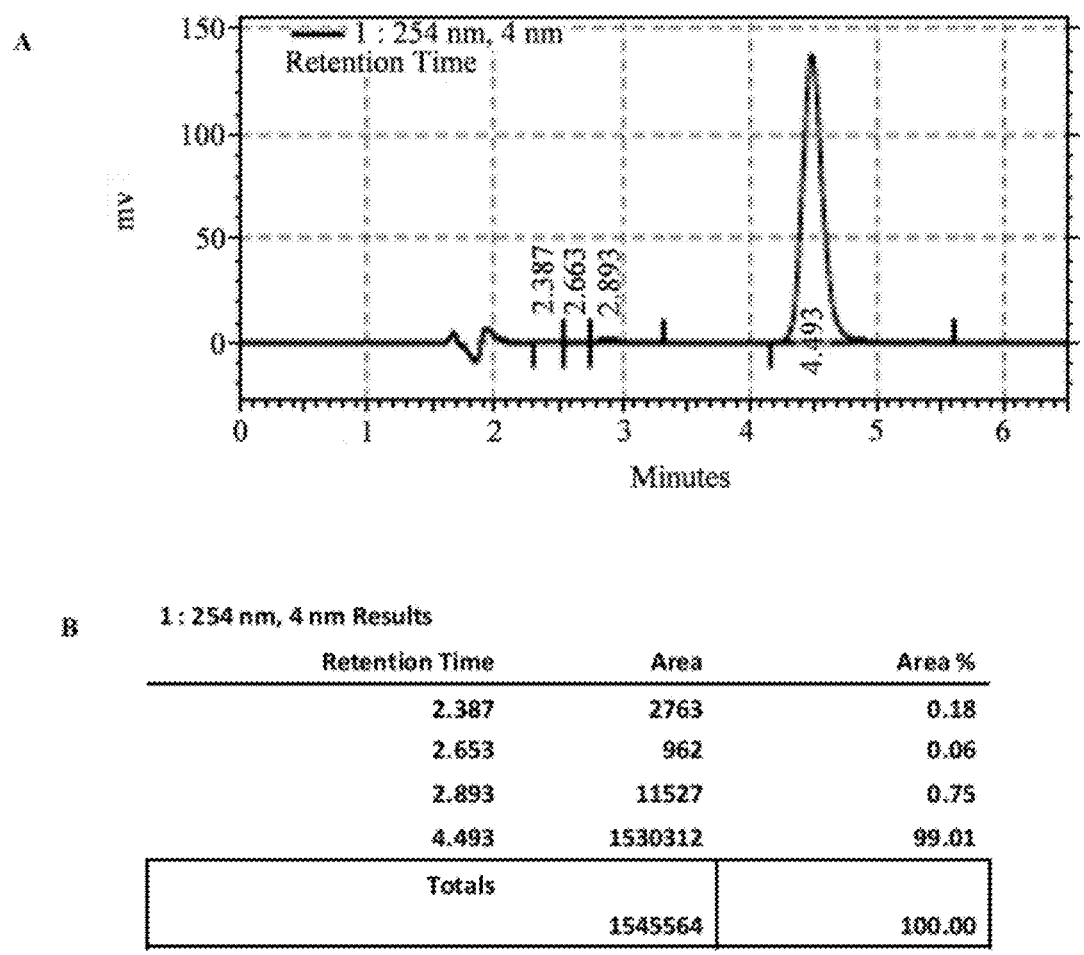
FIGS. 15(A) and (B) are HPLC data for compound 1. (A) HPLC graph results obtained using the following conditions; Column: Restek Ultra C18 5 µM 150 mM×4.6 mM; Method: 20% water in MeOH, flow rate 1.0 mL/min, $t_R$=4.6 min. Detector: Jasco MD-2010 plus Multiwavelength. (B) Quantitative analysis of the HPLC data obtained from (A).

(Z)-3-(2-(5-(N-(4-Fluorobenzyl)sulfamoyl)-2-oxoindolin-3-ylidene)hydrazinyl)benzoic acid methyl ester 1. Thionyl chloride (0.3 mL) was carefully added, dropwise and at 0° C., to a mixture of 4 (120 mg, 0.25 mmol) and methanol (1.5 mL) in a microwave tube (CEM, 5 mL size) equipped with a stirring bar. After the addition was completed, the tube was capped and heated in a CEM Discover microwave (Max-Power mode; run time: 5 minutes; hold time: 30 minutes; max pressure: 300 psi; stirring: on) at 85° C. for 30 minutes. The crude product which precipitated was collected by filtration (sintered funnel) and washed with methanol (2.0 mL). (NB:

metallic spatulas or other metallic tools should be avoided until all the thionyl chloride has been removed). The process was repeated 8 times and the products combined and redissolved in 100 mL THF. Removal of THF under vacuum afforded the ester 1 (922 mg, 85%) as a yellow solid; HPLC purity: 99.0% (C18 column; 20% water in MeOH, flow rate 1.0 mL/min, $t_R$=4.6 min). Esterification of the acid 4 gave the methyl ester 1 that was 99.0% pure as measured by HPLC. The analytical data of 1 ($^1$H NMR, $^{13}$C NMR, LC-MS) agrees with that previously reported Lawrence, et al., Inhibitors of Src homology-2 domain containing protein tyrosine phosphatase-2 (Shp2) based on oxindole scaffolds. J Med Chem 2008; 51:4948-56), as seen in FIG. 15.

Figure 16:
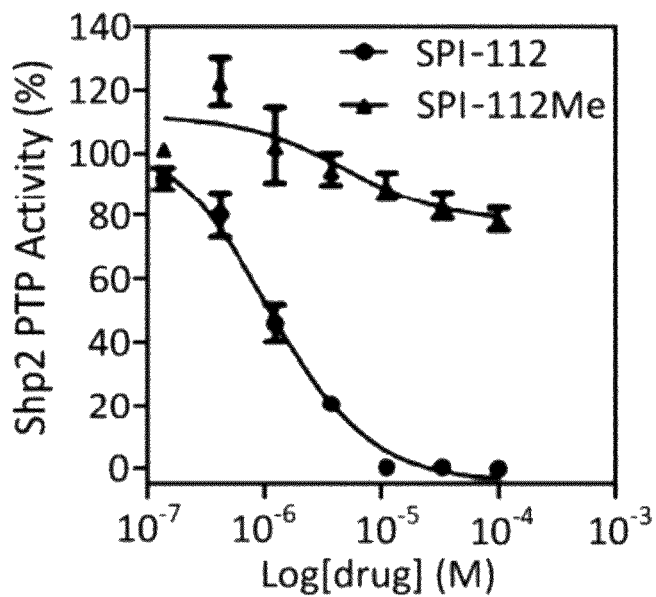
FIG. 16 is a graph showing a comparison of Shp2 PTP inhibition by SPI-112 and SPI-112Me in vitro. $IC_{50s}$ of SPI-112 and SPI-112Me on Shp2 PTP were determined in vitro using a GST-Shp2 PTP protein as the enzyme and DiFMUP as the substrate. The results were from three (SPI-112) and two (SPI-112Me) experiments performed in duplicates.
Figure 17:
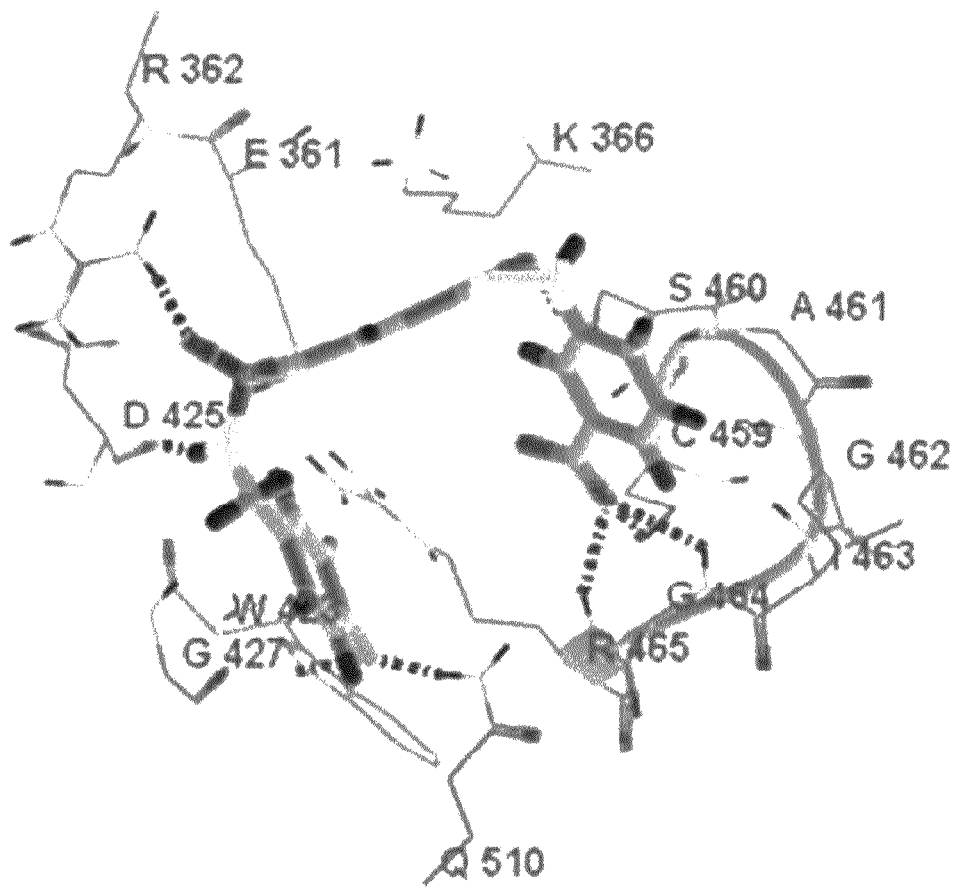
FIG. 17 is an illustration of a computer docking model of SPI-112 binding to the Shp2 PTP domain. Carbon atoms are colored medium grey, oxygen in dark grey (tips), nitrogen in light grey, hydrogen in black, and sulfur in grey-ish black. SPI-112 is shown in cylindrical representation. Amino acid residues of Shp2 are shown as lines. Grey-black dashed lines are predicted hydrogen bonds between SPI-112 and Shp2, which are shown schematically but not to scale. The hydrogen bonds are defined with a minimum donor angle of 120° and minimum acceptor angle of 90° and maximum length of 2.5 Å. The green loop identifies the catalytic P-loop of Shp2.
Figure 18:
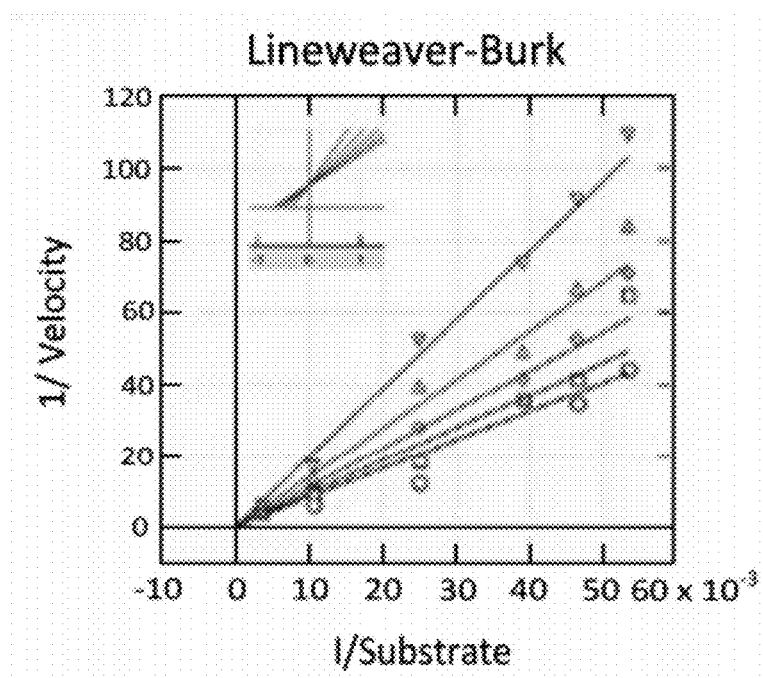
FIG. 18 is a Lineweaver-Burk plot of enzyme kinetics data of inhibition of the Shp2 PTP with SPI-112. The data were fit to competitive, noncompetitive and uncompetitive linear inhibition models with noncompetitive and uncompetitive model fits calculated with proportional weighting and using the Levenberg-Marquart Robust algorithm to minimize influence of any outliers in the data. The model was compared to the competitive model as the simplest model by Akaike's Information Criterion (AIC) evidence ratio since most models did not yield a Chi-square value for computing an F-value to run an F-test. The linear competitive model fit the best with a $K_i$ value of 0.8 µM±0.9 µM (SEM) and the lowest $AIC_c$ values with AIC ratios of $3.0 \times 10^8$ and 6.5 versus linear uncompetitive and noncompetitive, respectively, which are greatly statistically significant (AIC ratio>>2) in favor of the simpler model.

In vitro Shp2 PTP inhibition assay showed that, while SPI-112 potently inhibited Shp2 PTP ($IC_{50}$: 1.0 µM) as reported previously (Lawrence, et al., Inhibitors of Src homology-2 domain containing protein tyrosine phosphatase-2 (Shp2) based on oxindole scaffolds. J Med Chem 2008; 51:4948-56), the methyl ester analog did not inhibit Shp2 PTP ($IC_{50}$>100 µM), seen in FIG. 16. Computer modeling, shown in FIG. 17, suggested that SPI-112 binds to the catalytic pocket. The phenyl carboxylic acid points inwards mimicking a phosphotyrosine residue, forming hydrogen bonds with Gly-464 and Arg-465 of the P-loop, and this suggests that it is essential for binding and consequently the inhibitory activity. In agreement with the computer model, enzyme kinetic data obtained with SPI-112 were best fitted with the competitive inhibition model ($K_i$: 0.8 µM; seen in FIG. 18), suggesting that SPI-112 interacts with the catalytic site of Shp2.

Figure 19:
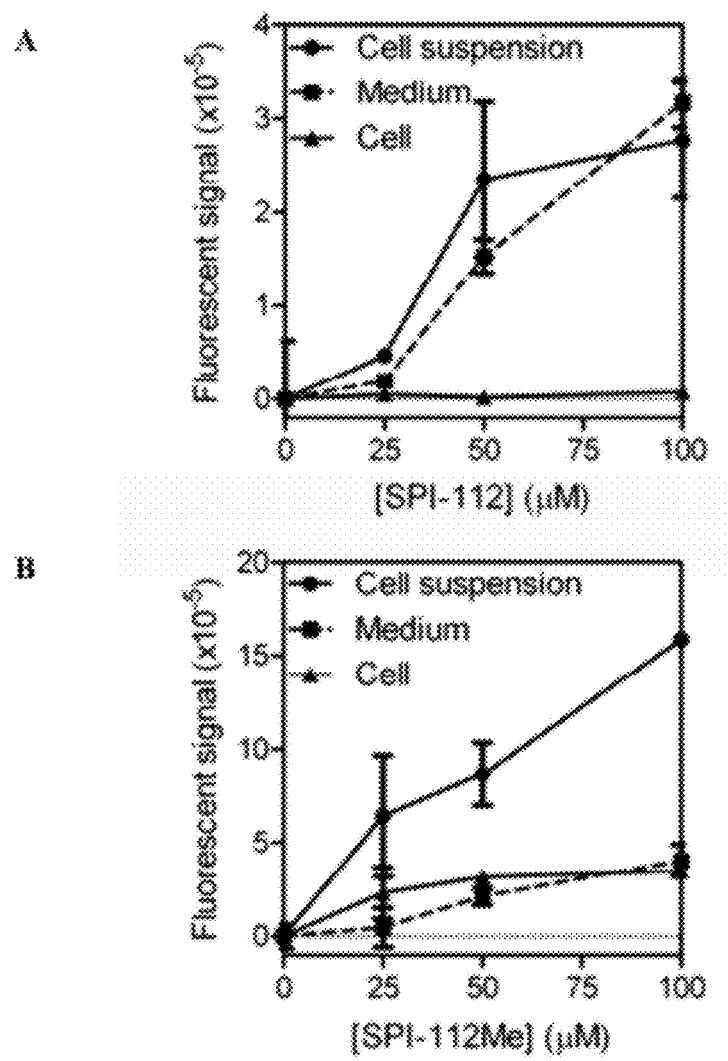
FIGS. 19(A) and (B) are graphs comparing SPI-112 and SPI-112Me fluorescence uptake into TF-1/Shp2$^{E76K}$ cells. TF-1/Shp2$^{E76K}$ cells were incubated with indicated concentrations of SPI-112 (A) or SPI-112Me (B) for 5 h. Fluorescent signals in cell culture suspension, cell-free medium, and cell pellet were measured. Total fluorescent signal in each sample was calculated and compared. The data were from a representative duplicate experiment (n=2) that had been repeated with similar data.

SPI-112 and SPI-112Me emitted concentration-dependent fluorescent signal under a Wallac 2100 EnVision multilable plate reader (PerkinElmer) at excitation/emission wavelengths of 485 nm/535 nm. This property provided a means for us to assess the cellular uptake of SPI-112 and SPI-112Me. TF-1/Shp2$^{E76K}$ cells were incubated with SPI-112 and SPI-112Me at different concentrations and then measured the fluorescent signal in cell culture, cell-free medium, and the cell pellets. When TF-1/Shp2$^{E76K}$ cells were incubated with SPI-112, essentially all fluorescent signal remained in the cell-free supernatants and only trace amount of fluorescent signal was associated with the cell pellets, see in FIG. 19(A). In contrast, when TF-1/Shp2$^{E76K}$ cells were incubated with SPI-112Me, with a substantial amount (21-36%) of fluorescent signal detected in the cells, seen in FIG. 19B). These results suggest that SPI-112Me, but not SPI-112, is able to enter cells.

Figure 20:
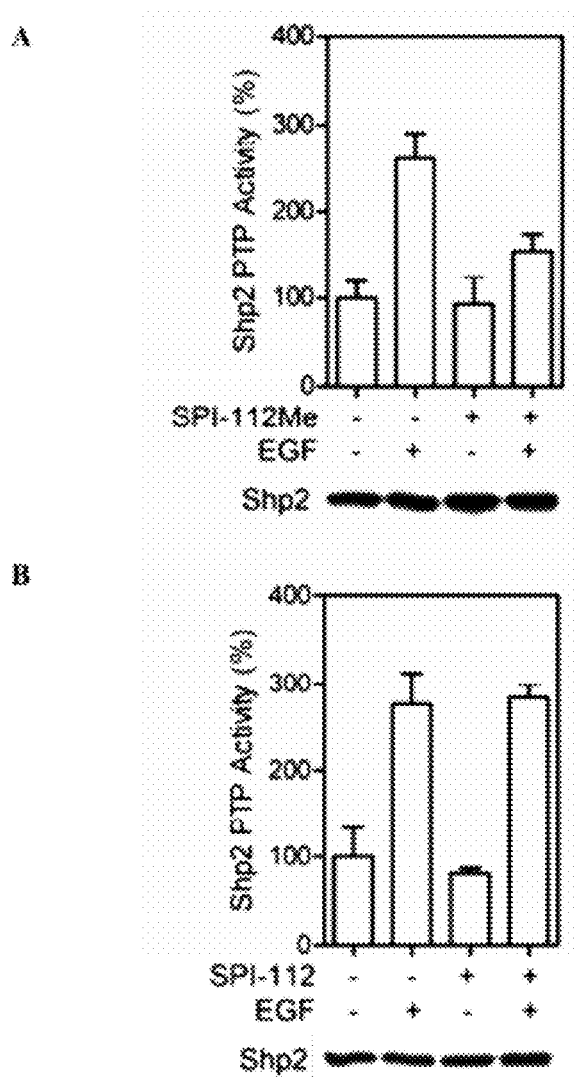
FIGS. 20(A) and (B) are graphs showing SPI-112Me suppresses Shp2 PTP activity in MDA-MB-468 cells. Sub-confluent MDA-MB-468 cells were serum-starved in DMEM/0.1% BSA for 18 h, pretreated overnight with (A) SPI-112Me (20 µM) or (B) SPI-112 (100 µM) and stimulated with EGF (50 ng/ml, 10 min) or mocked treated as indicated. Shp2 was immunoprecipitated from cell lysate supernatants and Shp2 PTP activity was measured. Data were from two experiments performed in duplicates. After the PTP reaction, a portion of each immunoprecipitate was used for immunoblotting with an anti-Shp2 antibody (lower panel).
Figure 21:
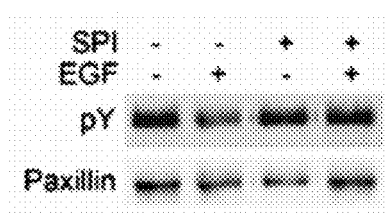
FIG. 21 is a blot showing Paxillin immunoprecipitated from serum-starved MDA-MB-468 cells treated with or without SPI-112Me (20 µM, 2 h) or EGF (50 ng/ml, 10 min) as indicated and analyzed by immunoblotting with antibody to phosphotyrosine (pY) or paxillin.
Figure 22:
FIG. 22 is a blot showing Erk1/2 staining from serum-starved MDA-MB-468 cells were pretreated with indicated concentrations of SPI-112Me and then stimulated with EGF (2 ng/ml, 5 min). Cell lysate supernatants were analyzed by immunoblotting with antibodies to phospho-Erk1/2 (pErk1/2) or total Erk1/2 (tErk1/2).
Figure 23:
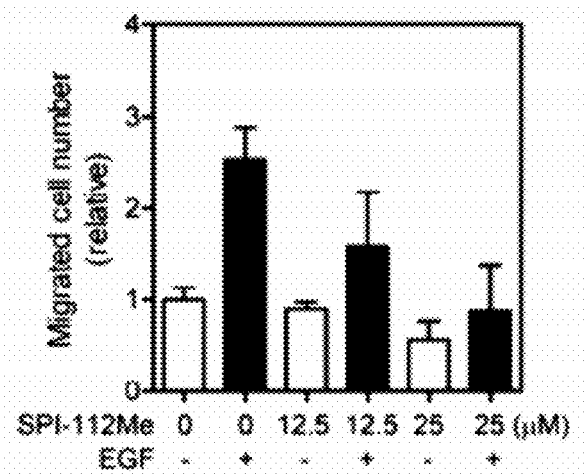
FIG. 23 is a graph showing transwell cell migration assay of MDA-MB-468 in the presence or absence of indicated concentrations of SPI-112Me and/or EGF (10 ng/ml). The data were from two duplicate experiments (n=4).

Shp2 is activated by EGF in MDA-MB-468 breast cancer cells. To test if SPI-112Me and SPI-112 are able to inhibit EGF-stimulated Shp2 in the cells, serum-starved MDA-MB-468 cells were pre-treated with or without SPI-112Me or SPI-112 and then stimulated with EGF. Shp2 was immunoprecipitated from cell lysate supernatants and its PTP activity was determined. Shp2 from EGF-stimulated cells had 2.6-fold higher PTP activity, seen in FIGS. 20(A) and (B). SPI-112Me (20 µM) pretreatment significantly reduced the EGF-stimulated Shp2 PTP activity by 77% (p=0.003), seen in FIG. 20(A). In contrast, SPI-112 did not affect the EGF-stimulated Shp2 PTP activity, seen in FIG. 20(B). Paxillin is a physiological substrate of Shp2 (Hellmuth, et al., Specific inhibitors of the protein tyrosine phosphatase Shp2 identified by high-throughput docking. Proc Natl Acad Sci USA 2008; 105:7275-80; Ren, et al., Roles of Gab1 and SHP2 in paxillin tyrosine dephosphorylation and Src activation in response to epidermal growth factor. J Biol Chem 2004; 279:8497-505; Manes, et al., Concerted activity of tyrosine phosphatase SHP-2 and focal adhesion kinase in regulation of cell motility. Mol Cell Biol 1999; 19:3125-35; Vadlamudi, et al., Differential regulation of components of the focal adhesion complex by heregulin: role of phosphatase SHP-2. J Cell Physiol 2002; 190:189-99). It was previously demonstrated that Shp2 dephosphorylates paxillin in EGF-stimulated MDA-MB-468 cells (Ren Y, Meng S, Mei L, Zhao Z J, Jove R, Wu J. Roles of Gab1 and SHP2 in paxillin tyrosine dephosphorylation and Src activation in response to epidermal growth factor. J Biol Chem 2004; 279:8497-505). Inhibition of EGF-stimulated paxillin dephosphorylation is an established surrogate marker of Shp2 inhibition (Hellmuth, et al., Specific inhibitors of the protein tyrosine phosphatase Shp2 identified by high-throughput docking. Proc Natl Acad Sci USA 2008; 105: 7275-80; Chen, et al., Discovery of a novel Shp2 protein tyrosine phosphatase inhibitor. Mol Pharmacol 2006; 70:562-70). Paxillin became dephosphorylated in EGF-stimulated cells, as seen in FIG. 21. Pretreatment of MDA-MB-468 cells with SPI-112Me prevented EGF-induced paxillin tyrosine dephosphorylation. Shp2 is known to mediate EGF-stimulated Erk1/2 activation. To determine if SPI-112Me is able to inhibit EGF-stimulated Erk1/2 activation, MDA-MB-468 cells were pre-treated with SPI-112Me at various concentrations (0-20 µM) and then stimulated with EGF. Erk1/2 activation was assessed by immunoblotting analysis of cell lysates with an antibody against the active, dual phosphorylated form of Erk1/2. Inhibition of EGF-stimulated pErk1/2 signal was observed at 10 µM SPI-112Me in this assay, seen in FIG. 22. Shp2 is involved in EGF-stimulated MDA-MB-468 cell migration. EGF-stimulated MDA-MB-468 cell migration was measured by the Transwell cell migration assay in the presence or absence of SPI-112Me, as seen in FIG. 23. EGF-increased MDA-MB-468 cell migration 2.5-fold, while EGF-stimulated MDA-MB-468 cell migration was reduced 62% by 12.5 µM SPI-112Me and was completed blocked in the presence of 25 µM SPI-112Me. These data indicate that SPI-112Me may inhibit Shp2 PTP activity in the EGF-stimulated MDA-MB-468 cells.

Figure 24:
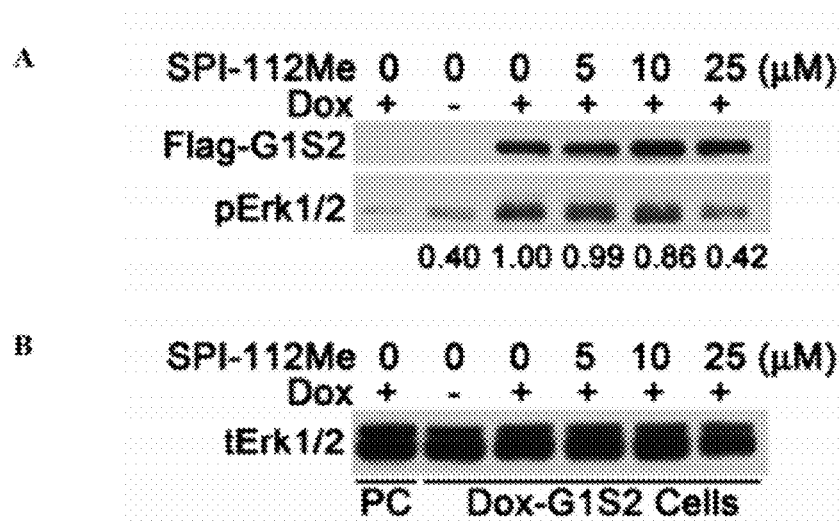
FIGS. 24(A) and (B) are blots showing SPI-112Me inhibits Erk2 activation by a Gab1-Shp2 chimera. Flp-In-T-Rex-293 cells (PC) or Flp-In-T-Rex-293 cells containing a dox-inducible Gab1PH-Shp2DN (Dox-G1S2) were incubated in serum-free medium, pretreated with indicated concentrations of SPI-112Me for 30 min and induced with dox. Cell lysates were prepared and analyzed by immunoblotting with antibodies to (A) Flag-tag, phospho-Erk1/2 (pErk1/2) and (B) total Erk1/2 (tErk12/). Numbers under the pErk1/2 panel indicate the relative signal intensity (average from two experiments).

To test the effects of SPI-112Me on Erk1/2 activation, SPI-112Me was introduced into a Gab1-Shp2 chimera. It was previously shown that expression of a fusion protein consisting of the Gab1 PH domain and an N—SH2 domain deletion mutant of Shp2 (Gab1PH-Shp2ΔN) caused constitutive Erk1/2 activation (Chen, et al., Discovery of a novel shp2 protein tyrosine phosphatase inhibitor. Mol Pharmacol 2006; 70:562-70; Cunnick, et al., Regulation of the mitogen-activated protein kinase signaling pathway by SHP2. J Biol Chem 2002; 277:9498-504). The Gab1PH-Shp2ΔN-induced Erk1/2 activation bypasses the up-stream growth factor receptor signaling steps. HEK293 cells containing dox-inducible Gab1PHShp2ΔN were generated using Flp-In-T-Rex-293 cells (Dox-G1S2). Dox-G1S2 cells which did not receive dox treatment did not express Flag-tagged Gab1PH-Shp2ΔN, and showed a low basal level of pErk1/2, as shown in FIGS. 24(A) and (B). Incubation of cells with dox induced Gab1PH-Shp2ΔN expression and activation of Erk1/2, whereas dox had no effect on Erk1/2 activation in the parental Flp-In-T-Rex-293 cells. Inhibition of Gab1PH-Shp2ΔN-induced Erk1/2 activation was observed in the presence of 10-25 µM SPI-112Me, seen in FIG. 24(A).

Figure 25:
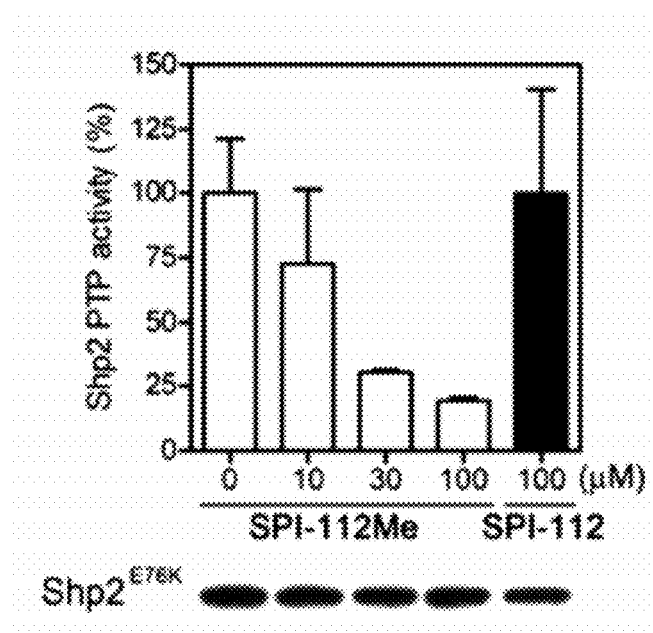
FIG. 25 is a graph showing Inhibition of Shp2E76K and Shp2E76K-induced Bcl-XL expression by SPI-112Me. TF-1/Shp2$^{E76K}$ cells were incubated in RPMI1640/10% FBS and treated with SPI-112Me or SPI-112 at the indicated concentrations. Shp2$^{E76K}$ was immunoprecipitated from cell lysates supernatant with an anti-Flag antibody and the PTP activity was determined. After the PTP reaction, a portion of each immunoprecipitate was used for immunoblotting with an anti-Shp2 antibody. Data were from two experiments.
Figure 26:
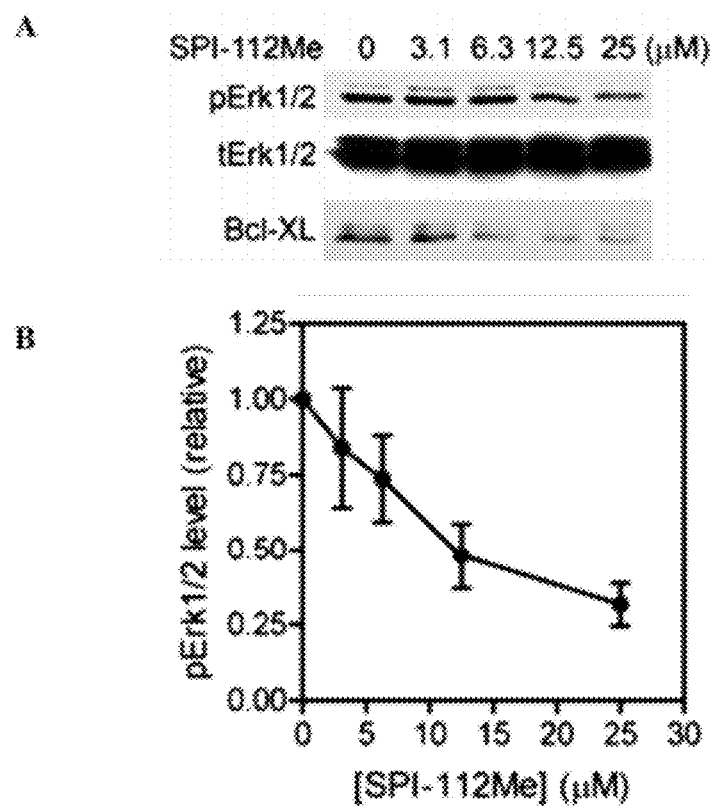
FIGS. 26(A) and (B) show inhibition of Shp2E76K and Shp2E76K-induced Bcl-XL expression by SPI-112Me. TF-1/Shp2$^{E76K}$ cells were incubated in RPMI1640/10% FBS with the indicated concentrations of SPI-112Me. (A) Cell lysates were analyzed by immunoblotting with antibodies to phospho-Erk1/2, total Erk1/2, or Bcl-XL. (B) The pErk1/2 signal intensities were quantified and graphed using the ImageQuant program (n=4).

SPI-112Me was introduced into leukemia-associated Shp2$^{E76K}$ TF-1 Cells. The gain-of-function Shp2E76K mutant has constitutively active PTP activity and is able to transform the cytokine-dependent TF-1 myeloid cells into cytokine-independence by upregulation of Bcl-XL through the Erk1/2 pathway (Ren, et al., Shp2E76K mutant confers cytokine-independent survival of TF-1 myeloid cells by up-regulating Bcl-XL. J Biol Chem 2007; 282:36463-73). To assess if Shp2$^{E76K}$ PTP activity was inhibited in SPI-112Me-treated TF-1/Shp2$^{E76K}$ cells, TF-1/Shp2$^{E76K}$ cells were incubated in GMCSF-free medium in the presence of different concentrations of SPI-112Me or a high concentration of SPI-112 (negative control). The Flag-tagged Shp2$^{E76K}$ was immunoprecipitated and the PTP activity was measured. Whereas there was no decrease in the Shp2$^{E76K}$ PTP activity in SPI-112-treated TF-1/Shp2$^{E76K}$ cells, lower Shp2$^{E76K}$ PTP activity was detected in SPI-112Me-treated TF-1/Shp2$^{E76K}$ cells, seen in FIG. 25. Shp2$^{E76K}$ activates Erk1/2 and up-regulates Bcl-XL in TF-1 cells to confer cytokine-independent cell survival. Consistently, immunoblotting analyses of cell lysates showed that SPI-112Me reduced the amounts of pErk1/2 and Bcl-XL in TF-1/Shp2E76K cells in a concentration-dependent manner, seen in FIGS. 26(A) and (B).

Figure 27:
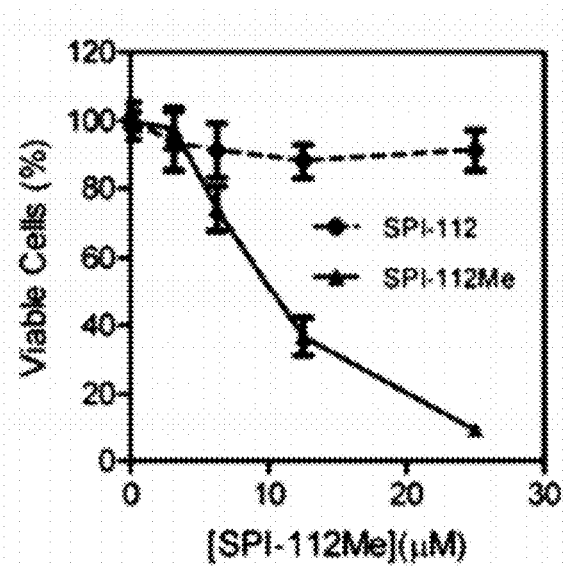
FIG. 27 is a graph showing SPI-112Me inhibits a gain-of-function Shp2 mutant-dependent survival of TF-1 cells. TF-1/Shp2$^{E76K}$ cells (1,000 cells/wells) were incubated in RPMI1640/10% FBS plus various concentrations of SPI-112 or SPI-112Me for 4 days and relative number of viable cells was measured with the CellTiterGlo reagent (Promega). The data were from two triplicate experiments.

To determine if SPI-112Me and SPI-112 affect Shp2$^{E76K}$-dependent cell growth, TF-1/Shp2$^{E76K}$ cells were cultured in GM-CSF-free medium in the presence of various concentrations of SPI-112Me or SPI-112 for 4 days and relative viable cell number was measured. SPI-112Me caused a concentration-dependent decrease in viable cells, seen in FIG. 27. A 50% decrease in viable TF-1/Shp2$^{E76K}$ cells was observed at 10 µM SPI-112Me in this assay. In contrast, SPI-112 did not affect TF-1/Shp2$^{E76K}$ cells, which is consistent with the notion that SPI-112 is not cell permeable.

Figure 28:
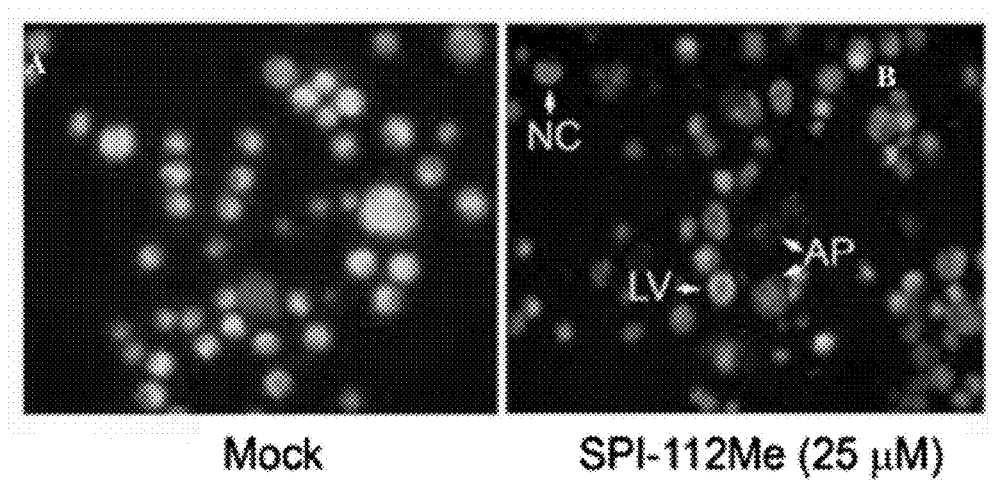
FIGS. 28(A) and (B) are representative images of immunohistochemistry nuclear stainings showing SPI-112Me inhibits a gain-of-function Shp2 mutant-dependent survival of TF-1 cells. TF-1/Shp2$^{E76K}$ cells were incubated in RPMI1640/10% FBS plus SPI-112Me as indicated for 3 days and then processed for EB/AO staining assay of apoptosis as described in the Materials and Methods.
Figure 29:
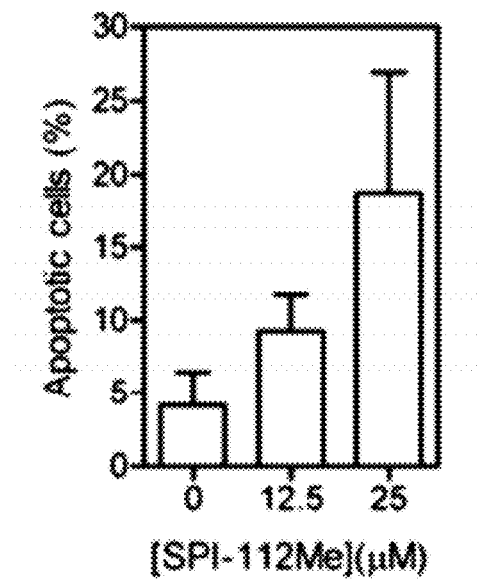
FIG. 29 is a graph showing SPI-112Me inhibits a gain-of-function Shp2 mutant-dependent survival of TF-1 cells. TF-1/Shp2$^{E76K}$ cells were incubated in RPMI1640/10% FBS plus SPI-112Me as indicated for 3 days and then processed for EB/AO staining assay of apoptosis as described in the Materials and Methods. Results show the percentage of apoptotic cells from 3 experiments.

The decrease in viable cell number could be due to inhibition of cell survival, cell proliferation, or both. An initial testing indicated that SPI-112Me-treated cells were fluorogenic under the laser light of flow cytometer, interfering with flow cytometric analysis of apoptosis. Therefore, a microscopic EB/AO staining assay (Ribble, et al., A simple technique for quantifying apoptosis in 96-well plates. BMC Biotechnol 2005; 5:12) was employed to examine apoptosis of SPI-112Me-treated TF-1/Shp2$^{E76K}$ cells. FIGS. 28(A) and (B) illustrate the nuclear morphology of EB/AO staining cells. As shown in FIG. 29, in the absence of SPI-112Me, there was an average of 4.2% of apoptotic cells. In the presence of 12.5 and 25 µM SPI-112Me, 9.3% and 18.8% of apoptotic cells were observed. Thus, SPI-112Me is able to inhibit Shp2$^{E76K}$-dependent survival of TF-1/Shp2$^{E76K}$ cells.

Figure 30:
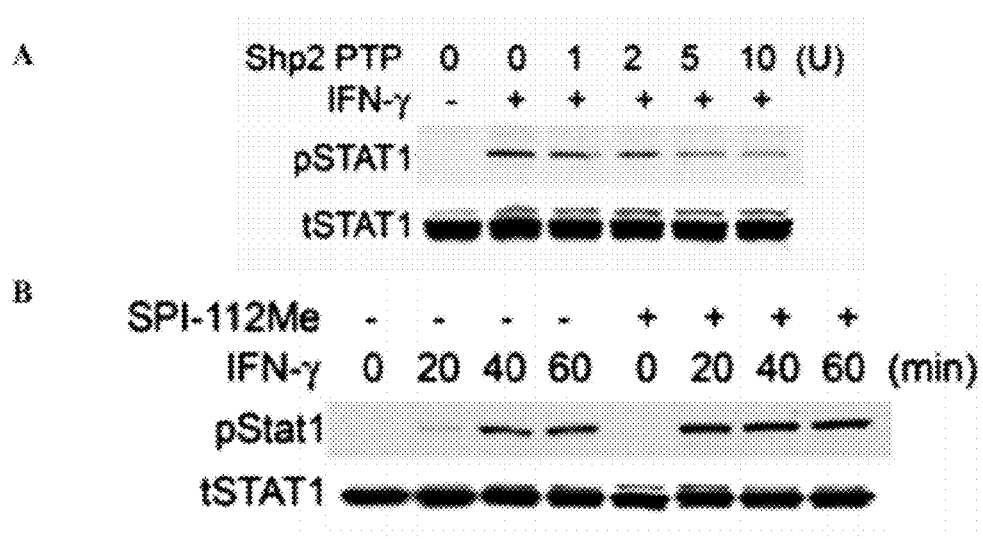
FIGS. 30(A) and (B) are blots showing SPI-112Me enhances the IFN-γ-induced esponses. (A) STAT1 was immunoprecipitated from HT-29 cells with or without IFN-γ stimulation and incubated with (A) a recombinant GST-Shp2 PTP in vitro as indicated. (B) HT-29 cells were pre-treated with or without SpI-112Me (20 □M, 2 h) and stimulated with IFN-□ (20 U/ml) for the indicated time. Cell lysates were analyzed by immunoblotting with antibodies to phospho-STAT1, total STAT1.

It was reported that STAT1 is a Shpt substrate (Wu, et al., SHP-2 is a dualspecificity phosphatase involved in Stat1 dephosphorylation at both tyrosine and serine residues in nuclei. J Biol Chem 2002; 277:47572-80) and increased IFN-stimulated STAT1 tyrosine phosphorylation was observed in mouse embryonic fibroblasts from Shp2 knockout mice (You, et al., Shp-2 tyrosine phosphatase functions as a negative regulator of the interferon-stimulated Jak/STAT pathway. Mol Cell Biol 1999; 19:2416-24). STAT1 from HT-29 cells treated with or without IFN-γ was immunoprecipitated. As shown in FIGS. 30(A) and (B), STAT1 tyrosine phosphorylation was induced by IFN-γ in HT-29 cells. Incubation of STAT1 isolated from IFN-γ-treated cells with GST-Shp2 PTP protein in vitro resulted in concentration-dependent STAT1 tyrosine dephosphorylation, supporting the notion that pSTAT1 is a Shp2 PTP substrate, as seen in FIG. 30(A). It was reasoned that if SPI-112Me inhibits Shp2 PTP in the cells, it would enhance the IFN-γ-stimulated STAT1 tyrosine phosphorylation. Indeed, comparison of STAT1 tyrosine phosphorylation in HT-29 cells stimulated with IFN-γ alone or with a combination of IFN-γ and SPI-112Me showed increased amount of tyrosine phosphorylated STAT1 in cells treated with both IFN-γ and SPI-112Me, seen in FIGS. 30(B) and 31. This results show that SPI-112Me was able to enhance the ability of IFN-γ to stimulate STAT1 tyrosine phosphorylation.

Figure 31:
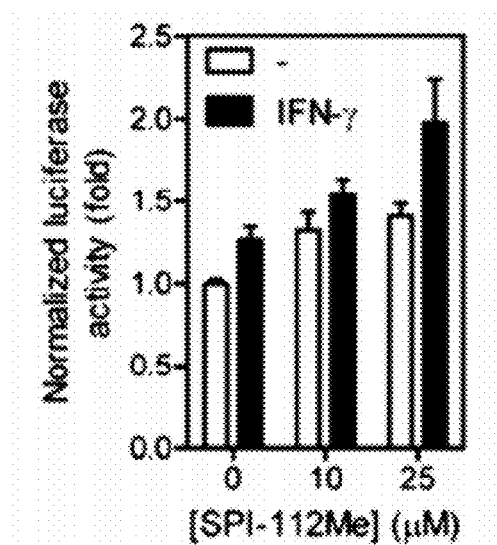
FIG. 31 is a graph showing SPI-112Me enhances the IFN-γ-induced responses. HT-29 cells were pre-treated with or without SpI-112Me (20 µM, 2 h) and stimulated with IFN-γ (20 U/ml) for the indicated time. Cell lysates were analyzed by immunoblotting with antibodies to phospho-STAT1, total STAT1, or β-actin.
Figure 32:
FIG. 32 is a blot showing SPI-112Me enhances the IFN-γ-induced responses. HT-29 cells co-transfected with pISRE-Luc and β-gal plasmids were pretreated with indicated concentrations of SPI-112Me for 2 h and then stimulated with 50 U/ml IFN-γ for 6 h. Luciferase activity was determined and normalized to β-galactosidase activity. Data were from two duplicate experiments (n=4).
Figure 33:
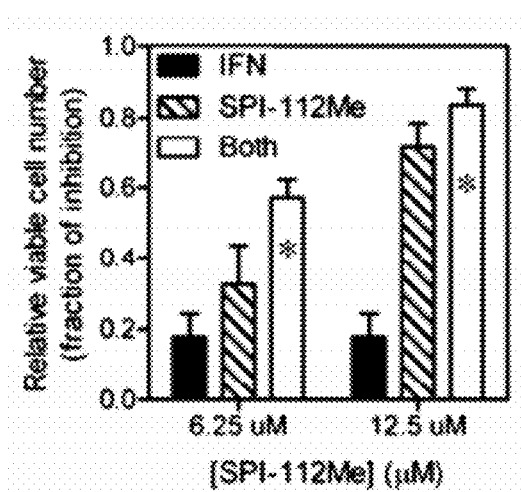
FIG. 33 is a graph showing SPI-112Me enhances the IFN-γ-induced responses. HT-29 cells were treated with or without SPI-1112Me (12.5 µM) and the indicated amounts of IFN-γ for 24 h. Cell lysates were analyzed by immunoblotting for the amounts of p21 and β-actin. HT-29 cells were plated in 96-well plates (1,000 cells/well) and incubated with IFN-γ (100 U/ml) and/or the indicated concentrations of SPI-112Me or vehicle control for 4 days. Viable cell number was measured. * indicates a synergistic effect. The data were from three experiments performed in triplicates (n=9).

To determine if SPI-112Me could enhance the STAT1-mediated transcription activity in response to a sub-saturated concentration of IFN-γ, HT-29 cells were transfected with pISRE-Luc and n-gal plasmids, stimulated with 50 U/ml IFN-γ in the presence or absence of SPI-112Me. IFN-γ alone activated the ISRE luciferase activity by 26%, which was further increased to 54% and 98% in the presence of 10 and 25 µM SPI-112Me, as seen in FIG. 31. It was reported that the cyclin-dependent kinase inhibitor p21 (CDKN1A) is a STAT1 target gene (Chin, et al., Cell growth arrest and induction of cyclin-dependent kinase inhibitor p21 WAF1/CIP1 mediated by STAT1. Science 1996; 272:719-22). As shown in FIG. 32, stimulation of HT-29 cells with IFN-γ increased p21 expression and higher levels of p21 were detected in HT-29 cells treated with both IFN-γ and SPI-112Me. To determine if SPI-112Me could enhance the anti-proliferative activity of IFN-γ, HT-29 cells were cultured in the presence or absence of 100 U/ml IFN-γ, 0-12.5 µM SPI-112Me, or combination of both agents for 4 days. Relative number of viable cells was measured and analyzed as fraction of inhibition, seen in FIG. 33. IFN-γ alone had a fraction of inhibition of 0.18. Similar to a previous report using a different Shp2 inhibitor, HT-29 cell growth was sensitive to inhibition of the Shp2 inhibitor. The fraction of inhibition caused by 6.25 and 12.5 µM SPI-112Me were 0.32 and 0.71, respectively. In the presence of both IFN-γ (100 U/ml) and SPI-112Me (6.25 and 12.5 µM), the fraction of inhibition increased to 0.57 and 0.84, respectively. Thus, IFN-γ and SPI-112Me displayed a synergistic effect on inhibition of HT-29 cell growth.

Though SPI-112 is among the most potent in vitro Shp2 inhibitors derived from NSC-117199, its lack of activity in intake cells precluded its use in biological studies. Conversly, the methyl ester prodrug described herein enhances the cellular uptake of SPI-112. In vitro Shp2 PTP inhibition assay indicated that SPI-112Me had very weak Shp2 PTP inhibitor activity ($IC_{50}$>100 µM). This is consistent with the computer docking data, which suggests that the carboxylic acid group is involved in the binding of SPI-112 to the Shp2 PTP catalytic site. Thus, neutralization of the negative charge of the carboxylic acid with the methyl group is predicted to hinder the inhibitory activity.

Figure 34:
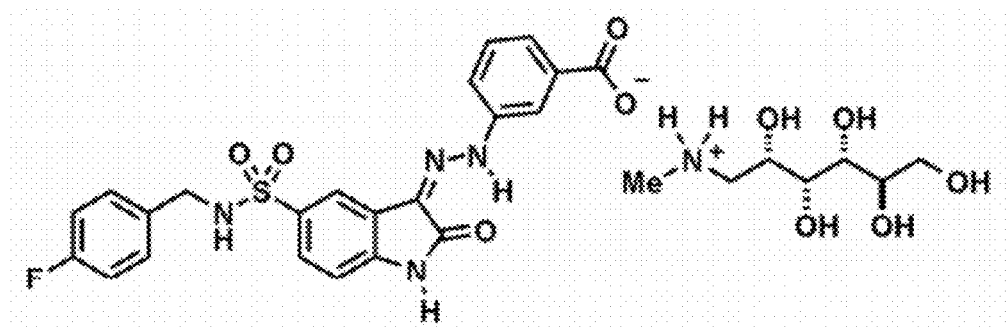
FIG. 34 is a diagram of the meglumine salt version of the selective Shp2 inhibitor SPI-112Me, labeled SPI-112-MEG.
Figure 35:
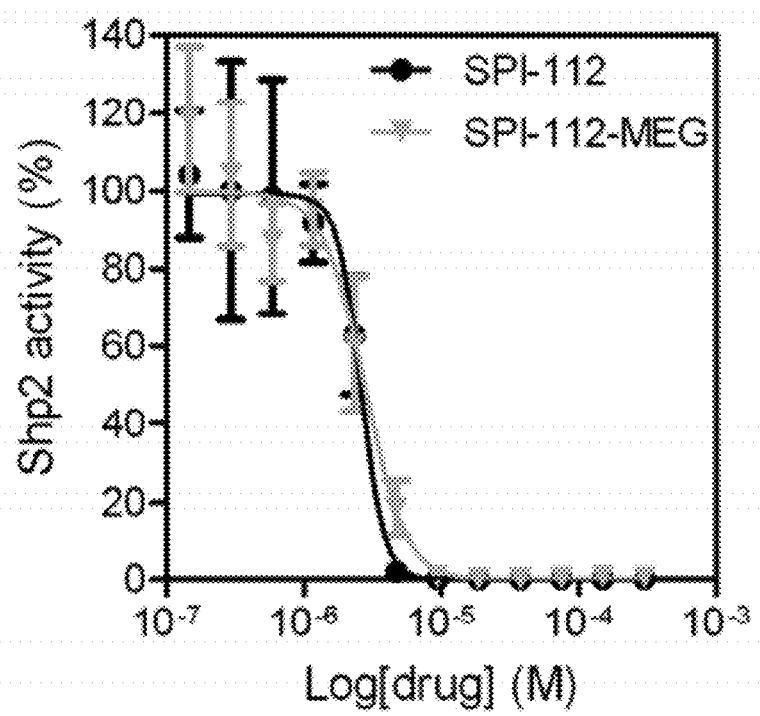
FIG. 35 is a graph showing the comparison of SPI-112 and SPI-112-MEG. Shp2 PTP inhibition assay was performed in vitro with SPI-112 and SPI-112-MEG. The data were from three independent experiments performed in duplicates (n=6). $IC_{50}$ derived from these data were: SPI-112: 2.6 µM, SPI-112-MEG: 2.8 µM.

Variations of the SPI-112Me compound were generated and tested to determine the effect of changing functional groups and moieties on the base compound. A meglumine salt-based variant, SPI-112-MEG, was generated as seen in FIG. 34. An Shp2 PTP inhibition assay was performed in vitro, comparing SPI-112 against SPI-112-MEG, with $IC_{50}$ of 2.6 µM for SPI-112, and 2.8 µM for SPI-112-MEG, as seen in FIG. 35. SPI-112-MEG therefore provides the benefits of SPI-112Me's cellular uptake with the activity of SPI-112.

Several lines of evidence showed that Shp2 PTP activity and function were inhibited in cells treated with SPI-112Me, indicating that SPI-112Me is a cell-active Shp2 PTP inhibitor. These include 1) inhibition of EGF-stimulated Shp2 PTP activity, paxillin dephosphorylation, Erk1/2 activation, and migration; 2) inhibition of Erk1/2 activation induced by an intracellular Gab1-Shp2 chimera; 3) inhibition of PTP activity of the leukemia-associated Shp2$^{E76K}$ mutant, Shp2$^{E76K}$-dependent Bcl-XL expression and cell survival; and 4) enhancement of IFN-γ-induced STAT1 tyrosine phosphorylation, STAT1-mediated transcription activity, and anti-proliferation activity. Together with the SPI-112Me fluorescent uptake experiment, these data indicate that SPI-112Me is able to enter cells and suggest that SPI-112Me is converted to the potent Shp2 inhibitor SPI-112 in the cells.

Shp2 mutants such as Shp2$^{E76K}$ are linked to several types of leukemias, particularly the deadly JMML. A transformation property of JMML cells is cytokine-independent growth. However, whether a Shp2 PTP inhibitor is sufficient to block Shp2 mutant-induced transformed phenotype in hematopoietic cells was not known. Although several reports have shown that the aryl sulfonic Shp2 inhibitor NSC-87877 that was previously identified is able to exert Shp2 inhibition activity in epithelial and neuronal cells (Zhan, et al., The protein tyrosine phosphatase SHP-2 is required for EGFRvIII oncogenic transformation in human glioblastoma cells. Exp Cell Res 2009; 315:2343-57; Chen, et al., Discovery of a novel shp2 protein tyrosine phosphatase inhibitor. Mol Pharmacol 2006; 70:562-70; Zhao, et al., Regulation of ACh receptor clustering by the tyrosine phosphatase Shp2. Dev Neurobiol 2007; 67:1789-801; Fuchikawa, et al., Protein tyrosine phosphatase SHP2 is involved in Semaphorin 4D-induced axon repulsion. Biochem Biophys Res Commun 2009; 385:6-10), it has no apparent activity in hematopoietic cells due to suspected poor uptake in hematopoietic cells. SPI-112Me represents the first cell-active Shp2 PTP inhibitor to display effectiveness of suppressing the PTP activity of a leukemia-associated Shp2 mutant and the Shp2 mutant-mediated cytokine-independence activity in hematopoietic cells.

While mutant Shp2 has been demonstrated as an oncogene in hematopoietic progenitor cells, it is not yet known whether mutant Shp2 is an oncogene in carcinomas. Shp2 mutations occur infrequently in carcinomas. Therefore, even if a gain-of-function Shp2 mutant can induce carcinomas, it is an uncommon event. However, the wildtype Shp2 is activated by oncogenic receptor tyrosine kinases such as ErbB and Met and is positively involved in their signaling. It will be very important to evaluate if Shp2 is required for the initiation and maintenance of malignant phenotypes induced by these oncogenic receptor tyrosine kinases and thus functions as a non-oncogene addiction gene (Luo, et al., Principles of cancer therapy: oncogene and nononcogene addiction. Cell 2009; 136:823-37) in carcinomas. The availability of SPI-112Me and other suitable Shp2 inhibitors should facilitate the evaluation of the role of Shp2 in carcinomas and the suitability of using a PTP inhibitor for cancer therapy.

It is demonstrate here that SPI-112Me can enhance IFN-γ signaling. This interesting finding not only provides a line of evidence that SPI-112Me is hitting the intended target (Shp2) in cancer cells but also reinforces the notion that SPI-112Me does not non-specifically impair the cellular signaling machinery or cell functions. This is because a global impairment of cellular functionality would likely prevent an increase in transcription activity. IFNs are noted for their anti-viral and anti-tumor activities but the use of high doses of IFNs is limited by toxicity. The development of SPI-112Me and other novel Shp2 inhibitors should facilitate the exploration of enhancing the anti-viral and anti-tumor efficacies of these biological agents at lower doses with a chemical inhibitor.

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a protein inhibitor, it will be apparent to those skilled in the art that variations and modifications are possible without deviating from the broad spirit and principle of the present invention. It is intended that all matters contained in the foregoing description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

TABLE 1

IC$_{50}$ values for indoline Shp2 inhibitors, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| XW2-038H 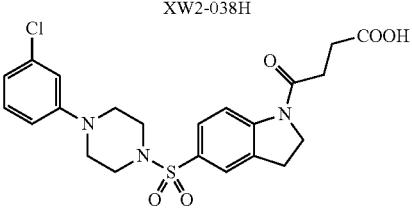 MW = 477.96 | 0.7 ± 0.3<br>n = 44 |
| XW2-125B 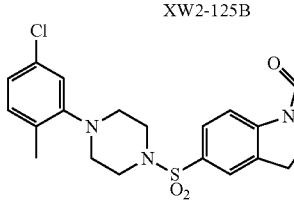 MW = 491.99 | 1.5 ± 0<br>n = 4 |
| JHE-02-001 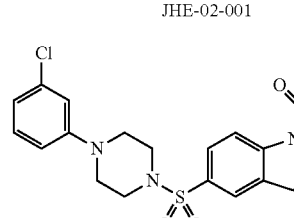 MW = 493.96 | 1.1 ± 0.3<br>n = 8 |
| JHE-02-119 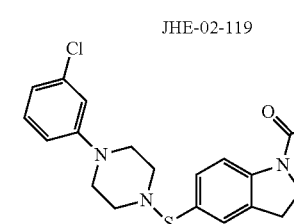 MW = 491.99 | 2.5 ± 0.5<br>n = 4 |
| JHE-02-067 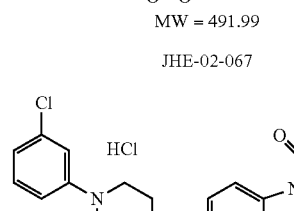 MW = 530.42<br>1.07 mg submitted on Jun. 30, 2008 | 1.3 ± 0.5<br>n = 3 |

TABLE 1-continued

IC$_{50}$ values for indoline Shp2 inhibitors, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| JHE-01-129A 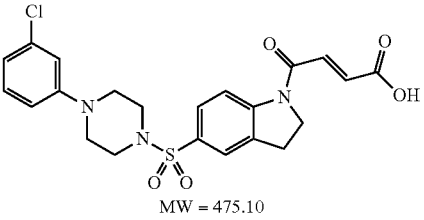 MW = 475.10 | 2.8 ± 0.7 n = 3 |
| JHE-02-032A 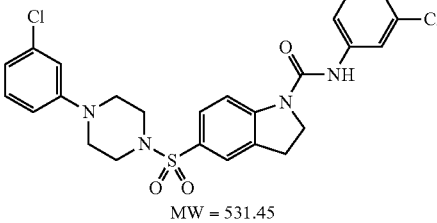 MW = 531.45 | 8.3 ± 3.4 n = 4 |
| JHE-02-065B 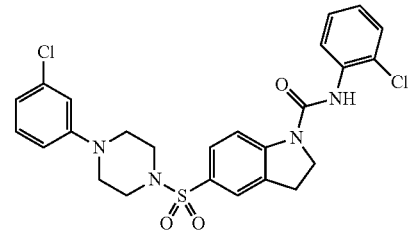 [SMILES: O=C(Nc1ccccc1Cl)N1CCc2cc(S(=O)(=O)N3CCN(c4cccc(Cl)c4)CC3)ccc21] MW = 531.45 | 3.2 ± 0.5 n = 4 |
| JHE-02-068B 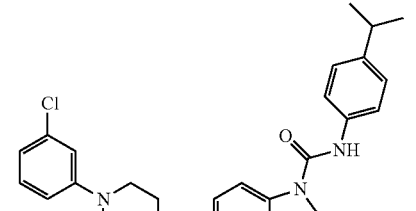 MW = 539.09 | 4.1 ± 1.0 n = 4 |
| XW3-002 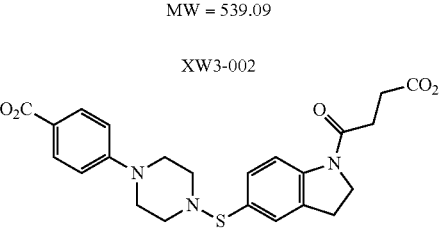 MW = 487.52 | 6.1 ± 1.8 n = 4 |
| JHE-02-068A 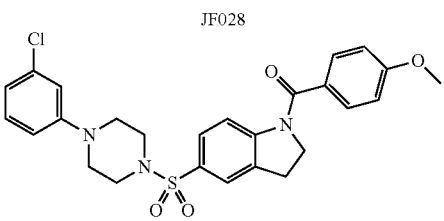 MW = 565.90 | 5.7 ± 2.5 n = 4 |
| JHE-01-129B 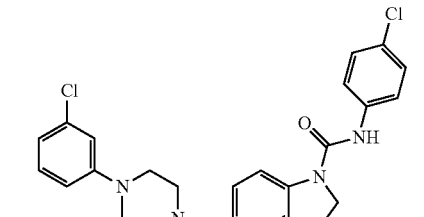 MW = 491.13 | 2.8 ± 0.7 n = 3 |
| JF028 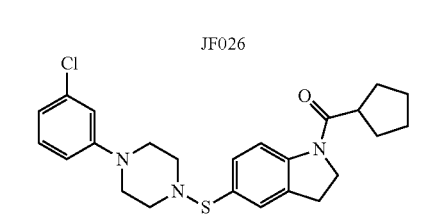 MW = 512.02 | 6.3 ± 2.9 n = 5 |
| JHE-02-065A 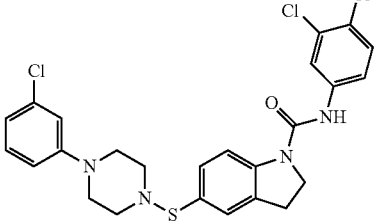 MW = 531.45 | 19.1 ± 5.1 n = 5 |
| JF026 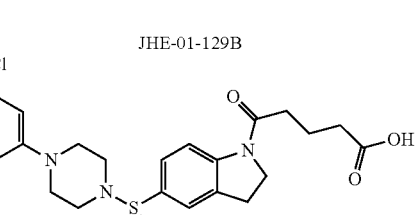 MW = 474.02 | 6.9 ± 2.2 n = 5 |

TABLE 1-continued

IC$_{50}$ values for indoline Shp2 inhibitors, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| JF020<br>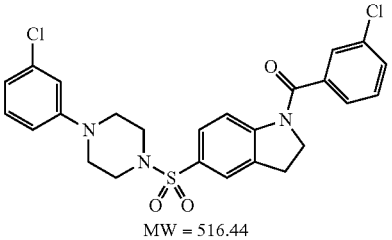<br>MW = 516.44 | 5.7 ± 3.9<br>n = 5 |
| JHE-01-137<br>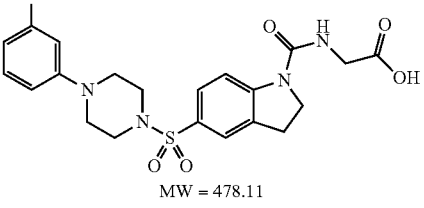<br>MW = 478.11 | 4.6 ± 0.3<br>n = 3 |
| JHE-02-033B<br>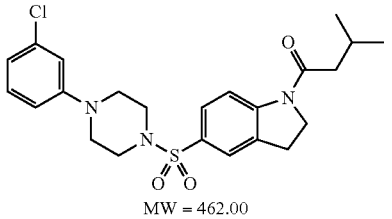<br>MW = 462.00 | 20.7 ± 10.8<br>n = 4 |
| JHE-02-038<br>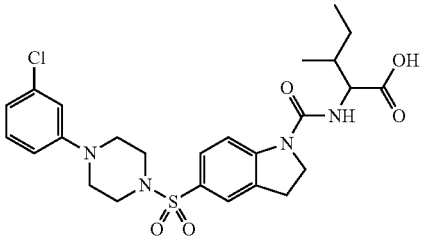 [SMILES: CCC(C)C(NC(=O)N1CCc2cc(S(=O)(=O)N3CCN(c4cccc(Cl)c4)CC3)ccc21)C(=O)O]<br>MW = 535.06 | 15.5 ± 7.5<br>n = 4 |
| JHE-02-032B<br>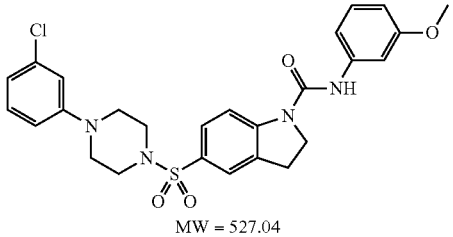<br>MW = 527.04 | 9.9 ± 3.5<br>n = 4 |
| JF025<br>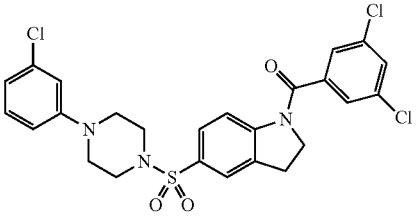 [SMILES: O=C(c1cc(Cl)cc(Cl)c1)N1CCc2cc(S(=O)(=O)N3CCN(c4cccc(Cl)c4)CC3)ccc21]<br>MW = 550.88 | 8.2 ± 2.6<br>n = 5 |
| JHE-02-063B<br>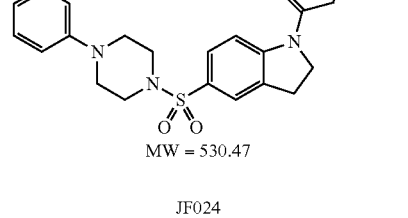<br>MW = 530.47 | 8.0 ± 1.9<br>n = 4 |
| JF024<br>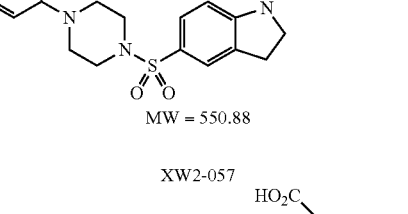<br>MW = 550.88 | 7.6 ± 1.3<br>n = 5 |
| XW2-057<br>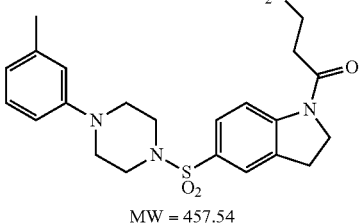<br>MW = 457.54 | 3.4 ± 2.3<br>n = 5 |
| XW2-124B<br>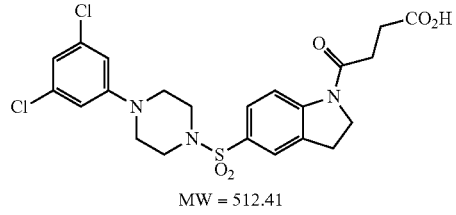<br>MW = 512.41 | 4.5 ± 1.2<br>n = 4 |

TABLE 1-continued

IC$_{50}$ values for indoline Shp2 inhibitors, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| JF038<br>MW = 515.00 | 12.6 ± 5.4<br>n = 5 |
| JHE-02-017B<br>MW = 492.98 | 6.4 ± 0.5<br>n = 5 |
| JF027<br>MW = 445.96 | 8.5 ± 2.0<br>n = 5 |
| XW2-119<br>MW = 579.51 | 9.1 ± 1.6<br>n = 4 |
| JHE-02-012<br>MW = 563.11 | 6.0 ± 2.8<br>n = 3 |
| XW2-036<br>MW = 512.41 | 4.6 ± 2.4<br>n = 7 |
| JHE-02-035A<br>MW = 512.02 | 8.1 ± 0.8<br>n = 4 |
| JF022<br>MW = 481.99 | 8.4 ± 2.3<br>n = 7 |
| JHE-02-017C<br>MW = 521.03 | 4.4 ± 1.9<br>n = 6 |
| JF023<br>MW = 550.88 | 7.1 ± 1.8<br>n = 6 |

TABLE 1-continued

IC$_{50}$ values for indoline Shp2 inhibitors, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| JF039<br>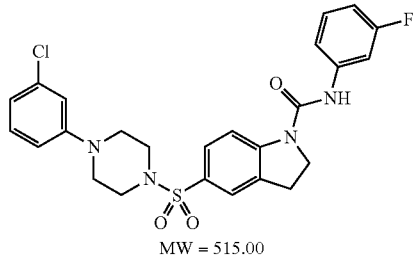<br>MW = 515.00 | 8.1 ± 1.7<br>n = 6 |
| JHE-02-069<br>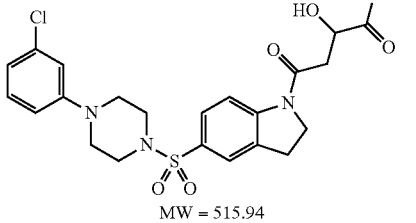<br>MW = 515.94 | 8.2 ± 0.4<br>n = 3 |
| JHE-02-010B<br>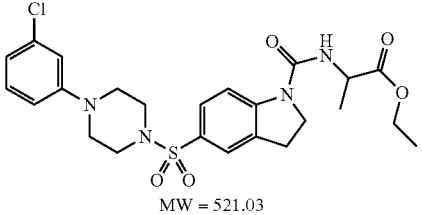<br>MW = 521.03 | 5.1 ± 2.7<br>n = 6 |
| JF040<br>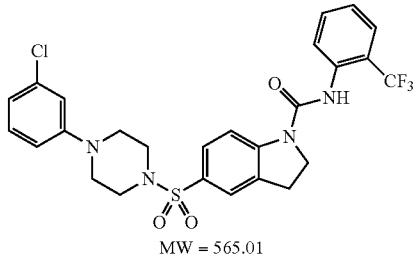<br>MW = 565.01 | 9.0 ± 1.7<br>n = 6 |
| JHE-01-155B<br>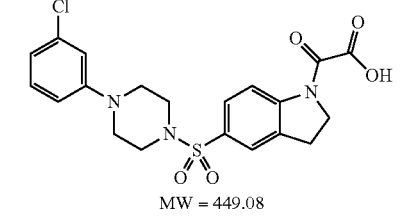<br>MW = 449.08 | 4.8 ± 2.8 |
| JF021<br>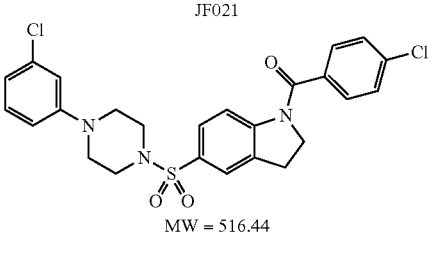<br>MW = 516.44 | 10.4 ± 2.0<br>n = 3 |
| JHE-02-033A<br>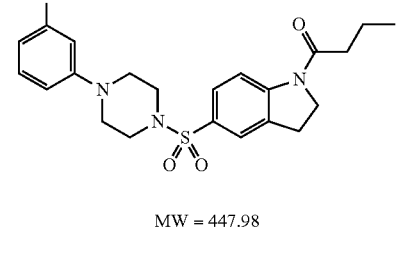<br>MW = 447.98 | 7.8 ± 2.1<br>n = 4 |
| JHE-02-017A<br>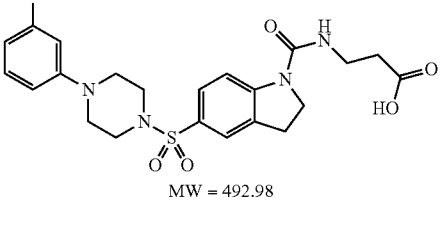<br>MW = 492.98 | 4.8 ± 3.3<br>n = 6 |
| JHE-02-010C<br>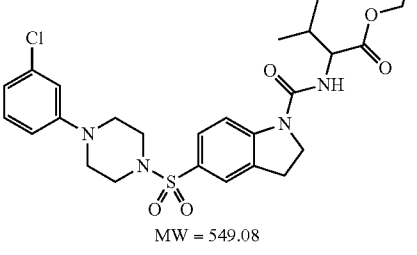<br>MW = 549.08 | 7.7 ± 2.4<br>n = 5 |
| JHE-02-019A<br>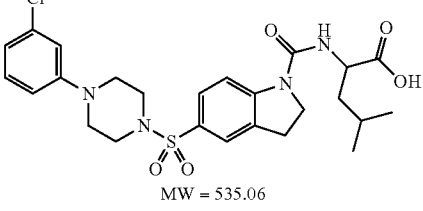<br>MW = 535.06 | 4.5 ± 3.5<br>n = 3 |

TABLE 1-continued

IC$_{50}$ values for indoline Shp2 inhibitors, as determined by in vitro phosphotyrosine phosphatase activity (DiFMUP) assay. Numerous batches were tested, as indicated by the batch number in column 1.

| Name, Structure, Molecular Weight | IC$_{50}$ (µM) |
| --- | --- |
| JF035<br>MW = 515.00 | 12.2 ± 2.0<br>n = 5 |
| XW2-038F<br>MW = 473.54 | 4.7 ± 4.4<br>n = 5 |
| JF033<br>MW = 497.01 | 11.7 ± 1.4<br>n = 5 |
| JHE-02-010A<br>MW = 521.03 | 9.3 ± 2.2<br>n = 5 |
| JHE-02-014<br>MW = 597.12 | 6.9 ± 4.2<br>n = 6 |
| JHE-02-029A<br>MW = 549.08 | 12.7 ± 0.7<br>n = 4 |
| XW2-031B<br>MW = 511.5 | 11.3 ± 3.1<br>n = 5 |
| JHE-02-020B<br>MW = 541.02 | 3.0 ± 0.8<br>n = 5 |
| XW2-124A<br>MW = 461.51 | 13.2 ± 3.6<br>n = 4 |
| JHE-02-020A<br>MW = 541.02 | 8.3 ± 5.6<br>n = 6 |

TABLE 1-continued

IC$_{50}$ values for indoline Shp2 inhibitors, as determined by in vitro phosphotyrosine phosphatase activity (DiFMUP) assay. Numerous batches were tested, as indicated by the batch number in column 1.

| Name, Structure, Molecular Weight | IC$_{50}$ (µM) |
|---|---|
| JHE-02-007<br>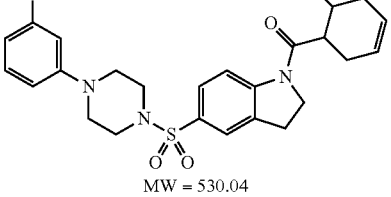<br>MW = 530.04 | 20.3 ± 4.3<br>n = 5 |
| XW2-038E<br>MW = 473.54 | 9.0 ± 5.9<br>n = 5 |
| JHE-02-019B<br>MW = 569.07 | 5.4 ± 2.7<br>n = 5 |
| JHE-02-015A<br>MW = 555.05 | 14.3 ± 4.1<br>n = 5 |
| XW3-006<br>MW = 478.96 | 16.6 ± 3.6 |
| JHE-01-169<br>MW = 449.95 | 9.6 ± 2.4<br>n = 5 |
| JF031<br>MW = 496.02 | 22.8 ± 4.5<br>n = 5 |
| JHE-02-117<br>MW = 487.92 | 47.0 ± 17.7<br>n = 4 |
| XW2-038A<br>MW = 443.52 | 14.8 ± 7.3<br>n = 5 |
| JHE-02-023<br>MW = 491.99 | 37.3 ± 5.3<br>n = 3 |

TABLE 1-continued

IC$_{50}$ values for indoline Shp2 inhibitors, as determined by in vitro phosphotyrosine phosphatase activity (DiFMUP) assay. Numerous batches were tested, as indicated by the batch number in column 1.

| Name, Structure, Molecular Weight | IC$_{50}$ (μM) |
|---|---|
| XW2-011B<br>MW = 461.5 | 31.9 ± 10.0<br>n = 5 |
| XW2-038D<br>MW = 461.51 | 34.6 ± 12.6<br>n = 4 |
| JHE-02-052<br>MW = 551.01 | 37.6 ± 13.8<br>n = 6 |
| JHE-01-134A<br>MW = 506.14 | 60.3 |
| XW2-038G<br>M.W. = 512.41 | 143.6 ± 89.5<br>n = 5 |

In the preceding specification, all documents, acts, or information disclosed does not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of a biomarker for cancer, it will be apparent to those skilled in the art that variations and modifications are possible without deviating from the broad spirit and principle of the present invention. It is intended that all matters contained in the foregoing description or shown in the accompanying drawings shall be interpreted as illustrative and not in a limiting sense. It is also to be understood that the following claims are intended to cover all of the generic and specific features of the invention herein described, and all statements of the scope of the invention which, as a matter of language, might be said to fall therebetween.

What is claimed is:

1. A compound having a formula (IV);

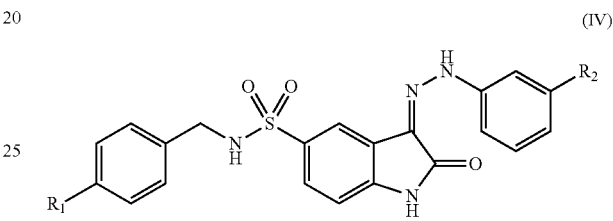

(IV)

wherein R$_1$ is F; and wherein R$_2$ is selected from the group consisting of COOCH$_3$, CO$_2$H, salts thereof, and CO$_2^-$·N$^+$H$_2$(CH$_3$)(CH$_2$CHOH)$_4$CH$_2$OH).

2. A method of treating a neoproliferative disease in an animal comprising the step of administering to a patient in need thereof an effective amount of a compound having the formula (V):

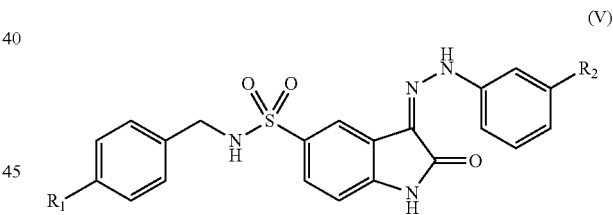

(V)

wherein R$_1$ is F; and wherein R$_2$ is selected from the group consisting of COOCH$_3$, CO$_2$H, salts thereof, and CO$_2^-$·N$^+$H$_2$(CH$_3$)(CH$_2$CHOH)$_4$CH$_2$OH);

wherein the neoproliferative disease is leukemia, glioblastoma, prostate cancer, lung cancer, gastric cancer, colorectal cancer, neuroblastoma, melanoma, or breast cancer.

3. The method of claim 2, further comprising administering a therapeutically effective amount of IFN-γ sequentially or in combination with the compound having the formula (V).

4. The method of claim 3, wherein the IFN is administered at 100 U/ml and the compound having the formula (V) is administered at between 6.25 μM and 12.5 μM.

5. The method of claim 2, wherein the leukemia is juvenile myelomonocytic leukemia, B-cell precursor acute lymphoblastic leukemia, chronic myelogenous leukemia, or acute myelogenous leukemia.

* * * * *

UNITED STATES PATENT AND TRADEMARK OFFICE
CERTIFICATE OF CORRECTION

PATENT NO. : 8,623,906 B2
APPLICATION NO. : 13/274699
DATED : January 7, 2014
INVENTOR(S) : Jie Wu et al.

Page 1 of 1

It is certified that error appears in the above-identified patent and that said Letters Patent is hereby corrected as shown below:

In the Specification

Column 1, Line 13 through Line 18 should read:
STATEMENT OF GOVERNMENT INTEREST
This invention was made with government support under grant number CA077467 awarded by the National Institutes of Health. The Government has certain rights in the invention.

Signed and Sealed this
Thirteenth Day of August, 2019

Andrei Iancu
*Director of the United States Patent and Trademark Office*